United States Patent [19]
Müller et al.

[11] Patent Number: 5,972,844
[45] Date of Patent: *Oct. 26, 1999

[54] SULPHONYLAMINO (THIO) CARBONYL-1, 2,4-TRIAZOLIN (THI) ONE DERIVATIVES AND THE USE THEREOF AS HERBICIDES

[75] Inventors: Klaus-Helmut Müller, Düsseldorf; Joachim Kluth, Langenfeld; Ernst Rudolf F Gesing, Erkrath; Klaus König, Odenthal; Markus Dollinger; Hans-Joachim Santel, both of Leverkusen, all of Germany

[73] Assignee: Bayer Aktiengesellschaft, Leverkusen, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/875,221

[22] PCT Filed: Jan. 15, 1996

[86] PCT No.: PCT/EP96/00141

§ 371 Date: Jul. 18, 1997

§ 102(e) Date: Jul. 18, 1997

[87] PCT Pub. No.: WO96/22982

PCT Pub. Date: Aug. 1, 1996

[30] Foreign Application Priority Data

Jan. 27, 1995 [DE] Germany .................. 195 02 579

[51] Int. Cl.⁶ .............. A01N 43/653; C07D 249/12
[52] U.S. Cl. .............. 504/273; 548/263.2; 548/263.4; 548/263.8; 548/264.6
[58] Field of Search .............. 504/273; 548/263.2, 548/263.4, 263.8, 264.6

[56] References Cited

U.S. PATENT DOCUMENTS

| | | | |
|---|---|---|---|
| 5,057,144 | 10/1991 | Daum et al. | 548/263.2 |
| 5,082,490 | 1/1992 | Müller et al. | |
| 5,085,684 | 2/1992 | Muller et al. | 71/92 |
| 5,238,910 | 8/1993 | Muller et al. | 504/273 |
| 5,300,480 | 4/1994 | Haas et al. | 548/263.4 |
| 5,356,865 | 10/1994 | Muller et al. | 504/273 |
| 5,488,028 | 1/1996 | Haas et al. | |
| 5,525,579 | 6/1996 | Kluth et al. | |
| 5,534,486 | 7/1996 | Müller et al. | |
| 5,652,372 | 7/1997 | Muller et al. | 548/263.4 |

FOREIGN PATENT DOCUMENTS

| | | |
|---|---|---|
| 0 294 666 A2 | 12/1988 | European Pat. Off. . |
| 0 341 489 | 11/1989 | European Pat. Off. . |
| 0 415 196 A2 | 3/1991 | European Pat. Off. . |
| 0 422 469 A2 | 4/1991 | European Pat. Off. . |
| 0 425 948 A2 | 5/1991 | European Pat. Off. . |
| 0 431 291 A2 | 6/1991 | European Pat. Off. . |
| 0 507 171 A1 | 10/1992 | European Pat. Off. . |
| 0 534 266 A1 | 3/1993 | European Pat. Off. . |
| 0 625 515 A1 | 11/1994 | European Pat. Off. . |

OTHER PUBLICATIONS

Angewandte Chemie, 81.Jahrgang, Heft 13, 1969, Seite 475–506.

Abstract 95:203841j; 28–Heterocycles Vo. 95, 1981, p. 673.

*Primary Examiner*—Patricia L. Morris
*Attorney, Agent, or Firm*—Sprung Kramer Schaefer & Briscoe

[57] ABSTRACT

The invention relates to sulphonylamino(thio)carbonyl-triazolin(ethi)ones of the general formula (I)

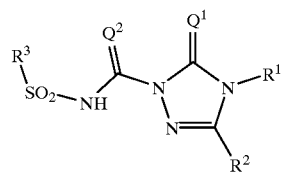

(I)

in which $Q^1$ represents oxygen or sulphur, $Q^2$ represents oxygen or sulphur, $R^1$ represents hydrogen, hydroxyl, amino, alkylidene-amino or a respectively optionally substituted radical from the group consisting of alkyl, alkenyl, alkinyl, alkoxy, alkenyloxy, alkylamino, dialkylamino, alkanoylamino, cycloalkyl, cycloalkylamino, cycloalkylalkyl, aryl and arylalkyl, $R^2$ represents hydrogen, hydroxyl, mercapto, amino, halogen or a respectively optionally substituted radical from the group consisting of alkyl, alkenyl, alkinyl, alkoxy, alkenyloxy, alkinyloxy, alkylthio, alkenylthio, alkinylthio, alkylamino, alkenylamino, alkinylamino, dialkylamino, alkanoylamino, aziridino, pyrrolidino, piperidino, morpholino, cycloalkyl, cycloalkenyl, cycloalkyloxy, cycloalkylthio, cycloalkylamino, cycloalkylalkyl, cycloalkylalkoxy, cycloalkylalkylthio, cycloalkylalkylamino, aryl, arylalkyl, aryloxy, arylalkoxy, arylthio, arylalkylthio, arylamino and arylalkylamino, or $R^1$ and $R^2$ together represent optionally branched alkanediyl, and $R^3$ represents respectively optionally substituted aryl, arylalkyl or heteroaryl, with the proviso that either $Q^1$ or $Q^2$ represents sulphur or both represent sulphur, and to salts of the compounds of the formula (I), furthermore to a plurality of processes for preparing the novel compounds of the formula (I) and the salts thereof and to the use of these compounds as herbicides.

4 Claims, No Drawings

SULPHONYL AMINO (THIO) CARBONYL-1, 2,4-TRIAZOLIN (THI) ONE DERIVATIVES AND THE USE THEREOF AS HERBICIDES

The invention relates to sulphonylamino(thio)carbonyl-triazolin(ethi)ones containing at least one thiocarbonyl group [—C(=S)—], to a plurality of processes for their preparation, and to their use as herbicides.

It is known that certain sulphonylaminocarbonyltriazolinones have herbicidal properties (cf. EP-A 341489, EP-A 422469, EP-A 425948, EP-A 431291). However, sulphonylamino(thio)carbonyl-triazolin(ethi)ones having at least one thiocarbonyl group have hitherto not been disclosed.

This invention, then, provides the novel sulphonylamino(thio)carbonyl-triazolin(ethi)ones of the general formula (I)

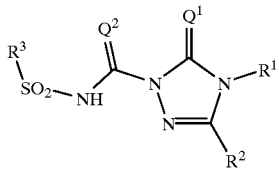

(I)

in which $Q^1$ represents oxygen or sulphur, $Q^2$ represents oxygen or sulphur, $R^1$ represents hydrogen, hydroxyl, amino, alkylideneamino or a respectively optionally substituted radical from the group consisting of alkyl, alkenyl, alkinyl, alkoxy, alkenyloxy, alkylamino, dialkylamino, alkanoylamino, cycloalkyl, cycloalkylamino, cycloalkylalkyl, aryl and arylalkyl, $R^2$ represents hydrogen, hydroxyl, mercapto, amino, halogen or a respectively optionally substituted radical from the group consisting of alkyl, alkenyl, alkinyl, alkoxy, alkenyloxy, alkinyloxy, alkylthio, alkenylthio, alkinylthio, alkylamino, alkenylamino, alkinylamino, dialkylamino, alkanoylamino, aziridino, pyrrolidino, piperidino, morpholino, cycloalkyl, cycloalkenyl, cycloalkyloxy, cycloalkylthio, cycloalkylamino, cycloalkylalkyl, cycloalkylalkoxy, cycloalkylalkylthio, cycloalkylalkylamino, aryl, arylalkyl, aryloxy, arylalkoxy, arylthio, arylalkylthio, arylamino and arylalkylamino, or $R^1$ and $R^2$ together represent optionally branched alkanediyl, and $R^3$ represents respectively optionally substituted aryl, arylalkyl or heteroaryl, with the proviso that either $Q^1$ or $Q^2$ represents sulphur or both represent sulphur, and salts of the compounds of the formula (I).

The novel sulphonylamino(thio)carbonyl-triazolin(ethi) ones of the general formula (I) are obtained when (a) triazolin(ethi)ones of the general formula (II)

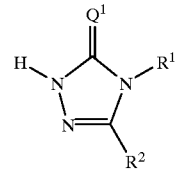

(II)

in which $Q^1$, $R^1$ and $R^2$ are each as described above, are reacted with sulphonyl iso(thio)cyanates of the general formula (III)

$$R^3\!-\!SO_2\!-\!N\!=\!C\!=\!Q^2 \qquad (III)$$

in which $Q^2$ and $R^3$ are each as described above, if appropriate in the presence of a reaction auxiliary and if appropriate in the presence of a diluent, or (b) triazolin(ethi)one derivatives of the general formula (IV)

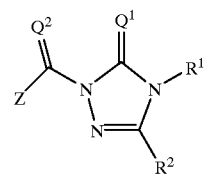

(IV)

in which $Q^1$, $Q^2$, $R^1$ and $R^2$ are each as described above and Z represents halogen, alkoxy, aryloxy or arylalkoxy, are reacted with sulphonamides of the general formula (V)

$$R^3\!-\!SO_2\!-\!NH_2 \qquad (V)$$

in which $R^3$ is as described above, if appropriate in the presence of an acid acceptor and if appropriate in the presence of a diluent, or (c) triazolin(ethi)ones of the general formula (II)

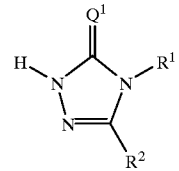

(II)

in which $Q^1$, $R^1$ and $R^2$ are each as described above, are reacted with sulphonamide derivatives of the general formula (VI)

$$R^3\!-\!SO_2\!-\!NH\!-\!CQ^2\!-\!Z \qquad (VI)$$

in which $Q^2$ and $R^3$ are each as described above and

Z represents halogen, alkoxy, aryloxy or arylalkoxy, if appropriate in the presence of an acid acceptor and if appropriate in the presence of a diluent, or (d) triazolin(ethi)ones of the general formula (II)

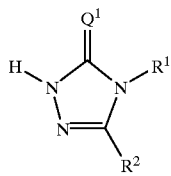

in which
$Q^1$, $R^1$ and $R^2$ are each as described above, are reacted with sulphonyl halides of the general formula (VII)

in which
$R^1$ is as described above and
X represents halogen,
and metal (thio)cyanates of the general formula (VIII)

in which
$Q^2$ is as described above and
M represents an alkali metal or an alkaline earth metal equivalent,
if appropriate in the presence of a reaction auxiliary and if appropriate in the presence of a diluent, and the compounds of the formula (I) obtained by processes (a), (b), (c) or (d) are, if desired, converted into salts by customary methods.

The novel sulphonylamino(thio)carbonyl-triazolin(ethi)ones of the general formula (I) have strong herbicidal action.

The invention preferably relates to compounds of the formula (I) in which $Q^1$ represents oxygen or sulphur, $Q^2$ represents oxygen or sulphur, $R^1$ represents hydrogen, hydroxyl or amino, or represents $C_2$–$C_{10}$-alkylideneamino or represents optionally fluorine-, chlorine-, bromine-, cyano-, $C_1$–$C_4$-alkoxy-, $C_1$–$C_4$-alkyl-carbonyl- or $C_1$–$C_4$-alkoxy-carbonyl-substituted $C_1$–$C_6$-alkyl, or represents respectively optionally fluorine-, chlorine- and/or bromine-substituted $C_2$–$C_6$-alkenyl or $C_2$–$C_6$-alkinyl, or represents respectively optionally fluorine-, chlorine-, cyano-, $C_1$–$C_4$-alkoxy- or $C_1$–$C_4$-alkoxy-carbonyl-substituted $C_1$–$C_6$-alkoxy, $C_1$–$C_6$-alkylamino or $C_1$–$C_6$-alkanoylamino, or represents $C_3$–$C_6$-alkenyloxy, or represents di-($C_1$–$C_4$-alkyl)-amino, or represents respectively optionally fluorine-, chlorine-, bromine-, cyano- and/or $C_1$–$C_4$-alkyl-substituted $C_3$–$C_6$-cycloalkyl, $C_3$–$C_6$-cycloalkylamino or $C_3$–$C_6$-cycloalkyl-$C_1$–$C_4$-alkyl, or represents respectively optionally fluorine-, chlorine-, bromine-, cyano-, nitro-, $C_1$–$C_4$-alkyl-, trifluoromethyl- and/or $C_1$–$C_4$-alkoxy-substituted phenyl or phenyl-$C_1$–$C_4$-alkyl, $R^2$ represents hydrogen, hydroxyl, mercapto, amino, fluorine, chlorine, bromine or iodine, or represents optionally fluorine-, chlorine-, bromine-, cyano-, $C_1$–$C_4$-alkoxy-, $C_1$–$C_4$-alkyl-carbonyl- or $C_1$–$C_4$-alkoxy-carbonyl-substituted $C_1$–$C_6$-alkyl, or represents respectively optionally fluorine-, chlorine- and/or bromine-substituted $C_2$–$C_6$-alkenyl or $C_2$–$C_6$-alkinyl, or represents respectively optionally fluorine-, chlorine-, cyano-, $C_1$–$C_4$-alkoxy- or $C_1$–$C_4$-alkoxy-carbonyl-substituted $C_1$–$C_6$-alkoxy, $C_1$–$C_6$-alkylthio, $C_1$–$C_6$-alkylamino or $C_1$–$C_6$-alkanoylamino, or represents $C_3$–$C_6$-alkenyloxy, $C_3$–$C_6$-alkinyloxy, $C_3$–$C_6$-alkenylthio, $C_3$–$C_6$-alkinylthio, $C_3$–$C_6$-alkenylamino or $C_3$–$C_6$-alkinylamino, or represents di-($C_1$–$C_4$-alkyl)-amino, or represents respectively optionally methyl- and/or ethyl-substituted aziridino, pyrrolidino, piperidino or morpholino, or represents respectively optionally fluorine-, chlorine-, bromine-, cyano- and/or $C_1$–$C_4$-alkyl-substituted $C_3$–$C_6$-cycloalkyl, $C_5$–$C_6$-cycloalkenyl, $C_3$–$C_6$-cycloalkyloxy, $C_3$–$C_6$-cycloalkylthio, $C_3$–$C_6$-cycloalkylamino, $C_3$–$C_6$-cycloalkyl-$C_1$–$C_4$-alkyl, $C_3$–$C_6$-cycloalkyl-$C_1$–$C_4$-alkoxy, $C_3$–$C_6$-cycloalkyl-$C_1$–$C_4$-alkylthio or $C_3$–$C_6$-cycloalkyl-$C_1$–$C_4$-alkylamino, or represents respectively optionally fluorine-, chlorine-, bromine-, cyano-, nitro-, $C_1$–$C_4$-alkyl-, trifluoromethyl- and/or $C_1$–$C_4$-alkoxy-substituted phenyl, phenyl-$C_1$–$C_4$-alkyl, phenoxy, phenyl-$C_1$–$C_4$-alkoxy, phenylthio, phenyl-$C_1$–$C_4$-alkylthio, phenylamino or phenyl-$C_1$–$C_4$-alkylamino, or $R^1$ and $R^2$ together represent optionally branched alkanediyl having 3 to 11 carbon atoms, and $R^3$ represents the grouping

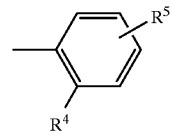

in which
$R^4$ and $R^5$ are identical or different and each represent hydrogen, fluorine, chlorine, bromine, iodine, nitro, $C_1$–$C_6$-alkyl (which is optionally substituted by fluorine, chlorine, bromine, cyano, carboxyl, $C_1$–$C_4$-alkoxycarbonyl, $C_1$–$C_4$-alkylamino-carbonyl, di-($C_1$–$C_4$-alkyl)-amino-carbonyl, hydroxyl, $C_1$–$C_4$-alkoxy, formyloxy, $C_1$–$C_4$-alkyl-carbonyloxy, $C_1$–$C_4$-alkoxy-carbonyloxy, $C_1$–$C_4$-alkylamino-carbonyloxy, $C_1$–$C_4$-alkylthio, $C_1$–$C_4$-alkylsulphinyl, $C_1$–$C_4$-alkylsulphonyl, di-($C_1$–$C_4$-alkyl)-aminosulphonyl, $C_3$–$C_6$-cycloalkyl or phenyl), or represent $C_2$–$C_6$-alkenyl (which is optionally substituted by fluorine, chlorine, bromine, cyano, $C_1$–$C_4$-alkoxy-carbonyl, carboxyl or phenyl), or represent $C_2$–$C_6$-alkinyl (which is optionally substituted by fluorine, chlorine, bromine, cyano, $C_1$–$C_4$-alkoxy-carbonyl, carboxyl or phenyl), or represent $C_1$–$C_4$-alkoxy (which is optionally substituted by fluorine, chlorine, bromine, cyano, carboxyl, $C_1$–$C_4$-alkoxy-carbonyl, $C_1$–$C_4$-alkoxy, $C_1$–$C_4$-alkylthio, $C_1$–$C_4$-alkylsulphinyl or $C_1$–$C_4$-alkylsulphonyl), or represent $C_1$–$C_4$-alkylthio (which is optionally substituted by fluorine, chlorine, bromine, cyano, carboxyl, $C_1$–$C_4$-alkoxy-carbonyl, $C_1$–$C_4$-alkylthio, $C_1$–$C_4$-alkylsulphinyl or $C_1$–$C_4$-alkylsulphonyl), or represent $C_2$–$C_6$-alkenyloxy (which is optionally substituted by fluorine, chlorine, bromine, cyano or $C_1$–$C_4$-alkoxy-carbonyl), or represent $C_2$–$C_6$-alkenylthio (which is optionally substituted by fluorine, chlorine, bromine, cyano, nitro, $C_1$–$C_3$-alkylthio or $C_1$–$C_4$-alkoxy-carbonyl), $C_3$–$C_6$-alkinyloxy, $C_3$–$C_6$-alkinylthio, or represent the radical —S(O)$_p$—R$^6$ in which p represents the numbers 1 or 2 and $R^6$ represents $C_1$–$C_4$-alkyl (which is optionally substituted by fluorine, chlorine, bromine, cyano or $C_1$–$C_4$-alkoxy-carbonyl), $C_3$–$C_6$-alkenyl, $C_3$–$C_6$-alkinyl, $C_1$–$C_4$-alkoxy, $C_1$–$C_4$-alkoxy-$C_1$–$C_4$-alkylamino, $C_1$–$C_4$-alkylamino, di-($C_1$–$C_4$-alkyl)-amino or phenyl, or represent the radical —NHOR$^7$ in which $R^7$ represents $C_1$–$C_{12}$-alkyl (which is optionally substituted by fluorine, chlorine, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl, $C_1$–$C_4$-alkoxy-carbonyl, $C_1$–$C_4$-alkylamino-carbonyl or di-($C_1$–$C_4$-alkyl)-amino-carbonyl), or represents $C_3$–$C_6$-alkenyl (which is optionally substituted by fluorine, chlorine or bromine), $C_3$–$C_6$-alkinyl, $C_3$–$C_6$-cycloalkyl, $C_3$–$C_6$-cycloalkyl-$C_1$–$C_2$-alkyl or phenyl-$C_1$–$C_2$-alkyl (which is optionally substituted by fluorine, chlorine, nitro, cyano, $C_1$–$C_4$-alkyl, $C_1$–$C_4$-alkoxy or $C_1$–$C_4$-alkoxy-carbonyl), or represents benzhydryl or represents phenyl (which is optionally substituted by fluorine, chlorine, nitro, cyano, $C_1$–$C_4$-alkyl, trifluoromethyl, $C_1$–$C_4$-alkoxy, $C_1$–$C_2$-fluoroalkoxy, $C_1$–$C_4$-alkylthio, trifluoromethylthio or $C_1$–$C_4$-alkoxy-carbonyl), $R^4$ and $R^5$ further represent phenyl or phenoxy, or represent $C_1$–$C_4$-alkyl-carbonylamino, $C_1$–$C_4$-alkoxy-carbonylamino, $C_1$–$C_4$-alkylamino-carbonyl-amino or di-($C_1$–$C_4$-alkyl)-amino-carbonylamino, or represent the radical —CO—$R^8$ in which $R^8$ represents hydrogen, $C_1$–$C_6$-alkyl, $C_3$–$C_6$-cycloalkyl, $C_1$–$C_6$-alkoxy, $C_3$–$C_6$-cycloalkoxy, $C_3$–$C_6$-alkenyloxy, $C_1$–$C_4$-alkylthio, $C_1$–$C_4$-alkylamino, $C_1$–$C_4$-alkoxyamino, $C_1$–$C_4$-alkoxy-$C_1$–$C_4$-alkyl-amino or di-($C_1$–$C_4$-alkyl)-amino (each of which is optionally substituted by fluorine and/or chlorine), $R^4$ and/or $R^5$ further represent trimethylsilyl, thiazolinyl, $C_1$–$C_4$-alkyl-sulphonyloxy or di-($C_1$–$C_4$-alkyl)-aminosulphonylamino, or represent the radical —CH=N—$R^9$ in which $R^9$ represents optionally fluorine-, chlorine-, cyano-, carboxyl-, $C_1$–$C_4$-alkoxy-, $C_1$–$C_4$-alkylthio-, $C_1$–$C_4$-alkylsulphinyl- or $C_1$–$C_4$-alkylsulphonyl-substituted $C_1$–$C_6$-alkyl, or represents optionally fluorine- or chlorine-substituted benzyl, or represents optionally fluorine- or chlorine-substituted $C_3$–$C_6$-alkenyl or $C_3$–$C_6$-alkinyl, or represents optionally fluorine-, chlorine-, bromine-, $C_1$–$C_4$-alkyl-, $C_1$–$C_4$-alkoxy-, trifluoromethyl-, trifluoromethoxy- or trifluoromethylthio-substituted phenyl, or represents optionally fluorine- and/or chlorine-substituted $C_1$–$C_6$-alkoxy, $C_3$–$C_6$-alkenyloxy, $C_3$–$C_6$-alkinyloxy or benzyloxy, or represents amino, $C_1$–$C_4$-alkylamino, di-($C_1$–$C_4$-alkyl)-amino, phenylamino, $C_1$–$C_4$-alkyl-carbonyl-amino, $C_1$–$C_4$-alkoxy-carbonylamino or $C_1$–$C_4$-alkyl-sulphonylamino, or represents optionally fluorine-, chlorine-, bromine- or methyl-substituted phenylsulphonylamino, furthermore, $R^3$ represents the radical

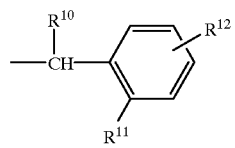

in which $R^{10}$ represents hydrogen or $C_1$–$C_4$-alkyl, $R^{11}$ and $R^{12}$ are identical or different and each represent hydrogen, fluorine, chlorine, bromine, nitro, cyano, $C_1$–$C_4$-alkyl (which is optionally substituted by fluorine and/or chlorine), $C_1$–$C_4$-alkoxy (which is optionally substituted by fluorine and/or chlorine), carboxyl, $C_1$–$C_4$-alkoxy-carbonyl, dimethylaminocarbonyl, $C_1$–$C_4$-alkylsulphonyl or di-($C_1$–$C_4$-alkyl)-aminosulphonyl; furthermore, $R^3$ represents the radical

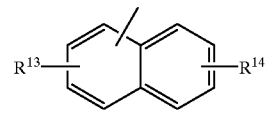

in which $R^{13}$ and $R^{14}$ are identical or different and each represent hydrogen, fluorine, chlorine, bromine, nitro, cyano, $C_1$–$C_4$-alkyl (which is optionally substituted by fluorine and/or chlorine) or $C_1$–$C_4$-alkoxy (which is optionally substituted by fluorine and/or chlorine); furthermore, $R^3$ represents the radical

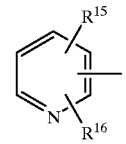

in which $R^{15}$ and $R^{16}$ are identical or different and each represent hydrogen, fluorine, chlorine, bromine, nitro, cyano, $C_1$–$C_4$-alkyl (which is optionally substituted by fluorine and/or chlorine), $C_1$–$C_4$-alkoxy (which is optionally substituted by fluorine and/or chlorine), or represent $C_1$–$C_4$-alkylthio, $C_1$–$C_4$-alkylsulphinyl or $C_1$–$C_4$-alkylsulphonyl (each of which is optionally substituted by fluorine and/or chlorine), or represent aminosulphonyl or mono-($C_1$–$C_4$-alkyl)-aminosulphonyl, or represent di-($C_1$–$C_4$-alkyl)-aminosulphonyl or $C_1$–$C_4$-alkoxy-carbonyl or dimethyl-aminocarbonyl; furthermore, $R^3$ represents the radical

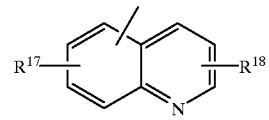

in which $R^{17}$ and $R^{18}$ are identical or different and each represent hydrogen, fluorine, chlorine, bromine, $C_1$–$C_4$-alkyl (which is optionally substituted by fluorine and/or bromine), $C_1$–$C_4$-alkoxy (which is optionally substituted by fluorine and/or chlorine), or represent $C_1$–$C_4$-alkylthio, $C_1$–$C_4$-alkylsulphinyl or $C_1$–$C_4$-alkylsulphonyl (each of which is optionally substituted by fluorine and/or chlorine), or represent di-($C_1$–$C_4$-alkyl)-aminosulphonyl; furthermore, $R^3$ represents the radical

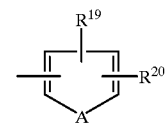

in which $R^{19}$ and $R^{20}$ are identical or different and each represent hydrogen, fluorine, chlorine, bromine, cyano, nitro, $C_1$–$C_4$-alkyl (which is optionally substituted by fluorine and/or chlorine), $C_1$–$C_4$-alkoxy (which is optionally substituted by fluorine and/or chlorine), $C_1$–$C_4$-alkylthio, $C_1$–$C_4$-alkylsulphinyl or $C_1$–$C_4$-alkylsulphonyl (each of which is optionally substituted by fluorine and/or chlorine), di-($C_1$–$C_4$-alkyl)-amino-sulphonyl, $C_1$–$C_4$-alkoxy-carbonyl or dimethylaminocarbonyl, and A represents oxygen, sulphur or the grouping N—$Z^1$ in which $Z^1$ represents hydrogen, $C_1$–$C_4$-alkyl (which is optionally substituted by fluorine, chlorine, bromine or cyano), $C_3$–$C_6$-cycloalkyl, benzyl, phenyl (which is optionally substituted by fluorine, chlorine, bromine or nitro), $C_1$–$C_4$-alkyl-carbonyl, $C_1$–$C_4$-alkoxy-carbonyl or di-($C_1$–$C_4$-alkyl)-amino-carbonyl; furthermore, $R^3$ represents the radical in which $R^{21}$ and $R^{22}$ are identical or different and each represent hydrogen, $C_1$–$C_4$-alkyl, halogen, $C_1$–$C_4$-alkoxy-carbonyl, $C_1$–$C_4$-alkoxy or $C_1$–$C_4$-halogenoalkoxy, $Y^1$ represents sulphur or the grouping N—$R^{23}$ in which $R^{23}$ represents hydrogen or $C_1$–$C_4$-alkyl; furthermore, $R^3$ represents the radical in which $R^{24}$ represents hydrogen, $C_1$–$C_4$-alkyl, benzyl, pyridyl, quinolinyl or phenyl, $R^{25}$ represents hydrogen, halogen, cyano, nitro, $C_1$–$C_4$-alkyl (which is optionally substituted by fluorine and/or chlorine), $C_1$–$C_4$-alkoxy (which is optionally substituted by fluorine and/or chlorine), dioxolanyl or $C_1$–$C_4$-alkoxy-carbonyl, and $R^{26}$ represents hydrogen, halogen or $C_1$–$C_4$-alkyl, and furthermore, $R^3$ represents one of the groupings listed below with the proviso that either $Q^1$ or $Q^2$ represents sulphur or that both represent sulphur.

The invention further preferably relates to the sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzyl-ammonium salts of compounds of the formula (I) in which $Q^1$, $Q^2$, $R^1$, $R^2$ and $R^3$ are preferably as defined above.

The invention in particular relates to compounds of the formula (I) in which $Q^1$ represents oxygen or sulphur, $Q^2$ represents oxygen or sulphur, $R^1$ represents hydrogen, hydroxyl or amino, or represents $C_3$–$C_8$-alkylideneamino or represents respectively optionally fluorine-, chlorine-, cyano-, methoxy- or ethoxy-substituted methyl, ethyl, n- or i-propyl, n-, i-, s- or t-butyl, or represents respectively optionally fluorine-, chlorine- or bromine-substituted propenyl, butenyl, propinyl or butinyl, or represents respectively optionally fluorine-, chlorine-, cyano-, methoxy- or ethoxy-substituted methoxy, ethoxy, n- or i-propoxy, n-, i-, s- or t-butoxy, methylamino, ethylamino, n- or i-propylamino, n-, i-, s- or t-butylamino, or represents propenyloxy or butenyloxy, or represents dimethylamino or diethylamino, or represents respectively optionally fluorine-, chlorine-, methyl- and/or ethyl-substituted cyclopropyl, cyclobutyl, cyclopentyl, cyclohexyl, cyclopropylamino, cyclobutylamino, cyclopentylamino, cyclohexyl-amino, cyclopropylmethyl, cyclobutylmethyl, cyclopentylmethyl or cyclohexylmethyl, or represents respectively optionally fluorine-, chlorine-, methyl-, trifluoromethyl- and/or methoxy-substituted phenyl or benzyl, $R^2$ represents hydrogen, hydroxyl, mercapto, amino, fluorine, chlorine or bromine, or represents respectively optionally fluorine-, chlorine-, cyano-, methoxy- or ethoxy-substituted methyl, ethyl, n- or i-propyl, n-, i-, s- or t-butyl, or represents respectively optionally fluorine-, chlorine- or bromine-substituted propenyl, butenyl, propinyl or butinyl, or represents respectively optionally fluorine-, chlorine-, cyano-, methoxy- or ethoxy-substituted methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, or represents propenyloxy, butenyloxy, propinyloxy, butinyloxy, propenylthio, butenylthio, propinylthio, butinylthio, propenylamino, butenylamino, propinylamino or butinylamino, or represents dimethylamino, diethylamino or dipropylamino, or represents respectively optionally fluorine-, chlorine-, methyl- and/or ethyl-substituted cyclopropyl, cyclobutyl, cyclopentyl, cyclohexyl, cyclopentenyl, cyclohexenyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents respectively optionally fluorine-, chlorine-, methyl-, trifluoromethyl- and/or methoxy-substituted phenyl, benzyl, phenoxy, benzyloxy, phenylthio, benzylthio, phenylamino or benzylamino, or $R^1$ and $R^2$ together represent optionally branched alkanediyl having 3 to 11 carbon atoms, and $R^3$ represents the radical

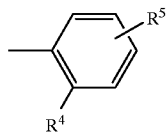

in which $R^4$ represents fluorine, chlorine or bromine, or represents respectively optionally fluorine- and/or chlorine-substituted methyl, ethyl, n- or i-propyl, or represents respectively optionally fluorine-, chlorine-, methoxy- or ethoxy-substituted methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, dimethylaminosulphonyl, diethylaminosulphonyl, N-methoxy-N-methylaminosulphonyl, methoxyaminosulphonyl, phenyl or phenoxy, or represents respectively optionally fluorine-, chlorine-, methoxy- or ethoxy-substituted methoxycarbonyl, ethoxycarbonyl, n- or i-propoxycarbonyl, and $R^5$ represents hydrogen, methyl, ethyl, fluorine, chlorine or bromine; furthermore, $R^3$ represents the radical

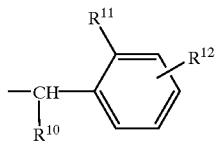

in which $R^{10}$ represents hydrogen, $R^{11}$ represents fluorine, chlorine, bromine, methyl, trifluoromethyl, methoxy, difluoromethoxy, trifluoromethoxy, ethoxy, methoxycarbonyl, ethoxycarbonyl, methylsulphonyl or dimethylaminosulphonyl, and $R^{12}$ represents hydrogen; furthermore, $R^3$ represents the radical

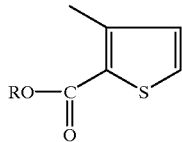

in which

R represents methyl, ethyl, n- or i-propyl, or $R^3$ represents the radical

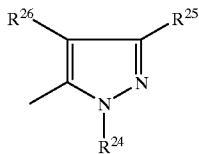

in which $R^{24}$ represents methyl, ethyl, n- or i-propyl, phenyl or pyridyl, $R^{25}$ represents hydrogen, fluorine, chlorine or bromine, $R^{26}$ represents fluorine, chlorine, bromine, methoxycarbonyl or ethoxycarbonyl, with the proviso that either $Q^1$ or $Q^2$ represents sulphur or that both represent sulphur.

The radical definitions listed above, whether general or in ranges of preference, apply not only to the end products of the formula (I) but also, correspondingly, to the starting materials and/or intermediates required in each case for the preparation. These radical definitions can be combined with one another as desired, thus including combinations between the preferred ranges indicated.

In the definitions of the radicals, hydrocarbon radicals such as alkyl, alkenyl or alkinyl, are, even in combination with heteroatoms, such as in alkoxy, alkylthio or alkylamino, even if this is not explicitly stated, straight-chain or branched.

Halogen generally represents fluorine, chlorine, bromine or iodine, preferably fluorine, chlorine or bromine, in particular fluorine or chlorine.

Examples of the meaning of the radicals $R^1$, $R^2$ and $R^3$ in the compounds of the formula (I) according to the invention are listed in the groups below.

Group 1

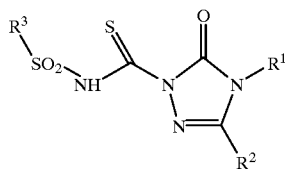

(IA)

$R^1$ has, for example, the meanings listed below: amino, n- or i-propylideneamino, methyl, ethyl, n- or i-propyl, n-, i-, s- or t-butyl, dichloropropyl, dibromopropyl, methoxypropyl, propenyl, butenyl, propinyl, butinyl, methoxy, ethoxy, n- or i-propoxy, methylamino, ethylamino, n- or i-propylamino, propenyloxy, dimethylamino, cyclopropyl, cyclobutyl, cyclopentyl, cyclohexyl, methyl-cyclopropyl or cyclopropylmethyl.

$R^2$ has, for example, the meanings listed below: hydrogen, chlorine, bromine, methyl, ethyl, n- or i-propyl, n-, i-, s- or t-butyl, trifluoromethyl, methoxymethyl, ethoxymethyl, propenyl, butenyl, propinyl, butinyl, methoxy, ethoxy, n- or i-propoxy, n-, i-, s- or t-butoxy, methylthio, ethylthio, n- or i-propylthio, n-, i-, s- or t-butylthio, fluoromethylthio, chloromethylthio, fluoroethylthio, chloroethylthio, difluoroethylthio, trifluoroethylthio, trifluoropropylthio, methylamino, ethylamino, n- or i-propylamino, n-, i-, s- or t-butylamino, propenyloxy, butenyloxy, propinyloxy, butinyloxy, propenylthio, butenylthio, propenylamino, butenylamino, propinylamino, butinylamino, dimethylamino, diethylamino, N-methyl-ethylamino, N-methyl-propylamino, N-ethyl-propylamino, cyclopropyl, cyclopropyloxy, cyclopropylamino, cyclopropylmethyl, cyclopropylmethoxy, cyclopropylmethylthio, phenyl, phenoxy, phenylthio, phenylamino, phenylmethyl, phenylmethoxy, phenylmethylthio or phenylmethylamino.

Additionally, $R^1$ and $R^2$ together have, for example, the following meanings: propane-1,3-diyl, butane-1,4-diyl, pentane-1,5-diyl, hexane-1,6-diyl, heptane-1,7-diyl and undecane-1,11-diyl.

$R^3$ has, for example, the meanings listed below: 2-fluoro-phenyl, 2-chloro-phenyl, 2-bromo-phenyl, 2,6-difluoro-phenyl, 2,6-dichloro-phenyl, 2-methyl-phenyl, 2-chloro-6- methyl-phenyl, 2-trifluoromethyl-phenyl, 2-(2-fluoro-ethyl)-phenyl, 2-(2-chloro-ethyl)-phenyl, 2-(3-fluoro-propyl)-phenyl, 2-(3-chloro-propyl)-phenyl, 2-(3,3,3-trifluoro-propyl)-phenyl, 2-(3,3,3-trifluoro-1-propenyl)-phenyl, 2-methoxy-phenyl, 2-ethoxy-phenyl, 2-difluoromethoxy-phenyl, 2-trifluoromethoxy-phenyl, 2-(2-fluoro-ethoxy)-phenyl, 2-(2-chloro-ethoxy)-phenyl, 2-(2-methoxy-ethoxy)-phenyl, 2-methylthio-phenyl, 2-ethylthio-phenyl, 2-methylsulphinyl-phenyl, 2-ethylsulphinyl-phenyl, 2-methylsulphonyl-phenyl, 2-ethylsulphonyl-phenyl, 2-dimethylaminosulphonyl-phenyl, 2-phenyl-phenyl, 2-methoxycarbonyl-phenyl, 2-ethoxycarbonyl-phenyl, 2-chloro-phenylmethyl, 2,6-dichloro-phenylmethyl, 2-difluoromethoxy-phenylmethyl, 2-trifluoromethoxy-phenylmethyl, 2-methoxycarbonyl-phenylmethyl, 2-ethoxycarbonyl-phenylmethyl, 2-methoxycarbonyl-3-thienyl, 2-ethoxycarbonyl-3-thienyl, 4-methoxycarbonyl-1-methyl-5-pyrazolyl, 4-ethoxycarbonyl-1-methyl-5-pyrazolyl, 3-chloro-4-methoxycarbonyl-1-methyl-5-pyrazolyl, 3-chloro-4-ethoxycarbonyl-1-methyl-5-pyrazolyl, 3-methoxycarbonyl-2-pyridyl, 3-ethoxycarbonyl-2-pyridyl, 3-dimethylaminocarbonyl-2-pyridyl, 3-methylsulphonyl-2-pyridyl or 3-ethylsulphonyl-2-pyridyl.

Group 2

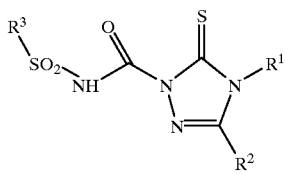
(IB)

$R^1$, $R^2$ and $R^3$ have, for example, the meanings listed above in group 1 under formula (IA).

Group 3

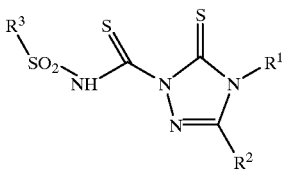
(IC)

$R^1$, $R^2$ and $R^3$ have, for example, the meanings listed above in group 1 under formula (IA).

Using, for example, 2,6-difluoro-phenyl isocyanate and 5-ethyl-4-methoxy-2,4-dihydro-3H-1,2,4-triazole-3-thione as starting materials, the course of reaction in the process (a) according to the invention can be illustrated by the following equation:

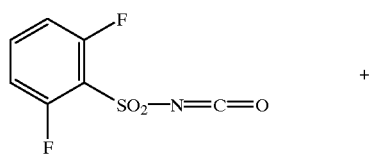

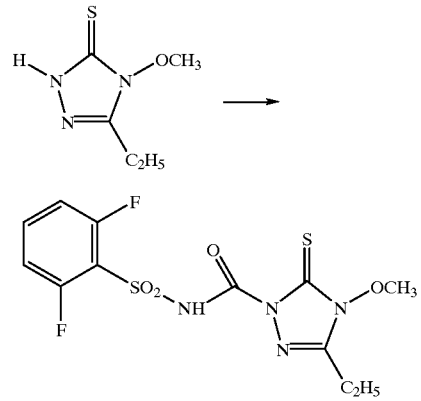

Using, for example, 2-methylthio-benzenesulphonamide and 2-chlorocarbonyl-4-dimethylamino-5-methyl-2,4-dihydro-3H-1,2,4-triazole-3-thiones starting materials, the course of reaction in the process (b) according to the invention can be illustrated by the following equation:

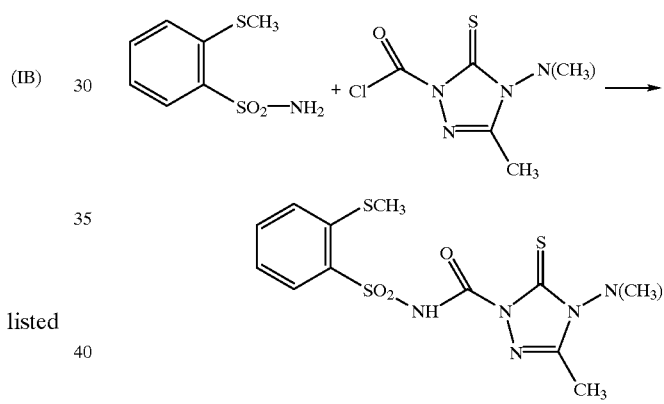

Using, for example, N-methoxythiocarbonyl-2-methoxy-benzenesulphonamide and 5-ethoxy-4-methyl-2,4-dihydro-3H-1,2,4-triazol-3-one as starting materials, the course of reaction in the process (c) according to the invention can be illustrated by the following equation:

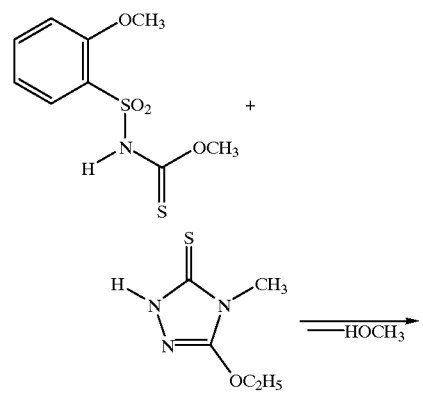

-continued

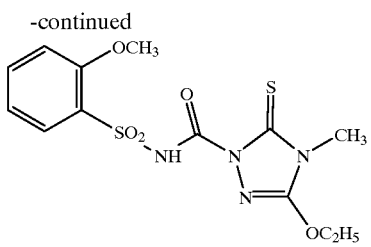

Using, for example, 4-ethyl-5-ethylthio-2,4-dihydro-3H-1,2,4-triazole-3-thione and 2-bromo-benzenesulphonyl chloride and potassium thiocyanate as starting materials, the course of reaction in the process (d) according to the invention can be illustrated by the following equation:

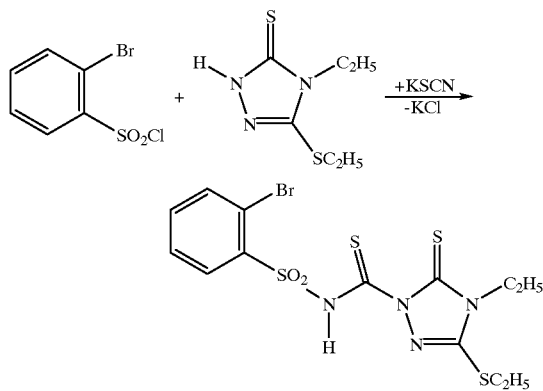

A general definition of the triazolin(ethi)ones to be used as starting materials in the processes (a), (c) and (d) according to the invention for preparing compounds of the formula (I) is given by the formula (II).

In the formula (II), $Q^1$, $R^1$ and $R^2$ each preferably or in particular have that meaning which has already been indicated above, in connection with the description of the compounds of the formula (I) according to the invention, as being preferable or particularly preferable for $Q^1$, $R^2$ and $R^2$.

The triazolin(ethi)ones of the general formula (II) are known and/or can be prepared by methods known per se (cf. Arch. Pharm. 301 (1968), 827; loc. cit. 307 (1974), 889; Bull. Soc. Chim. France 1962, 1365; loc. cit. 1975, 1191; Chem. Ber. 90 (1957), 909–921; loc. cit. 98 (1965), 3025–3099; loc. cit. 102 (1969), 755; J. Heterocycl. Chem. 15 (1978), 237–240; J. Indian Chem. Soc. 6 (1929), 565; Liebigs Ann. Chem. 637 (1960), 135; Monatshefte Chemie 123 (1992), 257; Tetrahedron 32 (1976), 2347–2352; Helv. Chim. Acta 63 (1980), 841–859; J. Chem. Soc. C 1967, 746–751; loc. cit. 1970, 26–34; J. Chem. Soc. Perkin I 1973, 2644; Fen Fak. Derg., Seri A (Ege Univ.) 7 (1984), 1–6—quoted in Chem. Abstracts 101:90846m; EP-A 283876; EP-A 294666; EP-A 298371; EP-A 301946; EP-A 305844; EP-A 341489; EP-A 362633; EP-A 370293; EP-A 391187; EP-A 398096; EP-A 398097; EP-A 399294; EP-A 415196; EP-A 422469; EP-A 425948; EP-A 431291; EP-A 477646; EP-A 502307; EP-A 503437; EP-A 505819; EP-A 511569; EP-A 513621; DE-A 2336827; DE-A 3839206; DE-A 3916208; DE-A 3916930; DD-P 64970; WO-A 93/04050; Preparation Examples).

A general definition of the sulphonyl iso(thio)cyanates also to be used as starting materials in the process (a) according to the invention for preparing compounds of the formula (I) is given by the formula (III).

In the formula (III), $Q^2$ and $R^3$ each preferably or in particular have that meaning which has already been indicated above, in connection with the description of the compounds of the formula (I) according to the invention as being preferable or particularly preferable for $Q^2$ and $R^3$.

The starting materials of the formula (III) are known and/or can be prepared by methods known per se (cf. U.S. Pat. No. 4,127,405, U.S. Pat. No. 4,169,719, U.S. Pat. No. 4,371,391, EP-A 7687, EP-A 13480, EP-A 21641, EP-A 23141, EP-A 23422, EP-A 30139, EP-A 35893, EP-A 44808, EP-A 44809, EP-A 48143, EP-A 51466, EP-A 64322, EP-A 70041, EP-A 173312).

A general definition of the triazolin(ethi)one derivatives to be used as starting materials in the process (b). according to the invention for preparing compounds of the general formula (I) is given by the formula (IV). In the formula (IV), $Q^1$, $Q^2$, $R^1$ and $R^2$ each preferably or in particular have that meaning which has already been indicated above, in connection with the description of the compounds of the formula (1), as being preferable or particularly preferable for $Q^1$, $Q^2$, $R^1$ and $R^2$; Z preferably represents fluorine, chlorine, bromine, methoxy, ethoxy, benzyloxy, phenoxy, halogeno- or nitro-phenoxy, and in particular represents methoxy, phenoxy or 4-nitro-phenoxy.

The starting materials of the formula (IV) have not been disclosed in the literature; as novel substances, they are also part of the subject matter of the present application. The novel compounds of the general formula (IV) are obtained when triazolin(ethi)ones of the general formula (II)

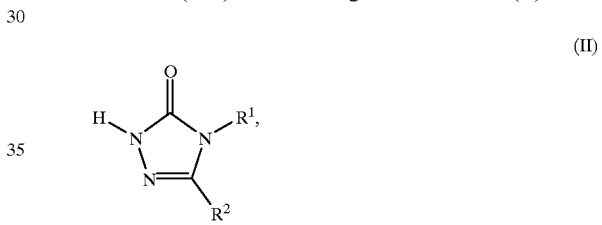

(II)

in which
$Q^1$, $R^1$ and $R^2$ are each as defined above,
are reacted with (thio)carbonic acid derivatives of the general formula (IX)

$$Z—CQ^2—Z^1 \quad (IX)$$

in which
Z and $Q^2$ are each as defined above and
$Z^1$ represents halogen, alkoxy, aralkoxy or aryloxy, if appropriate in the presence of an acid acceptor, such as, for example, sodium hydroxide or potassium hydroxide, sodium t-butoxide or potassium t-butoxide, and if appropriate in the presence of a diluent, such as, for example, methylene chloride, tetrahydrofuran or dimethoxyethane and/or water, at temperatures between 0° C. and 100° C.

A general definition of the sulphonamides also to be used as starting materials in the process (b) according to the invention for preparing compounds of the general formula (I) is given by the formula (V). In the formula (V), $R^3$ preferably or in particular has that meaning which has already been indicated above, in connection with the description of the compounds of the formula (I), as being preferable or particularly preferable for $R^3$.

The starting materials of the formula (V) are known and/or can be prepared by methods known per se (cf. U.S. Pat. No. 4,127,405, U.S. Pat. No. 4,169,719, U.S. Pat. No. 4,371,391, EP-A 7687, EP-A 13480, EP-A 21641, EP-A 23141, EP-A 23422, EP-A 30139, EP-A 35893, EP-A 44808, EP-A 44809, EP-A 48143, EP-A 51466, EP-A 64322, EP-A 70041, EP-A 173312).

A general definition of the sulphonamide derivatives to be used as starting materials in the process (c) according to the invention for preparing compounds of the general formula (I) is given by the formula (VI). In the formula (VI), $Q^2$ and $R^3$ each preferably or in particular have that meaning which has already been indicated above, in connection with the description of the compounds of the formula (I), as being preferable or particularly preferable for $Q^2$ and $R^3$; Z preferably represents fluorine, chlorine, bromine, methoxy, ethoxy, benzyloxy or phenoxy, and in particular represents methoxy or phenoxy.

The starting materials of the formula (VI) are known and/or can be prepared by methods known per se.

A general definition of the sulphonyl halides to be used as starting materials in the process (d) according to the invention for preparing compounds of the formula (I) is given by the formula (VII). In the formula (VII), $R^3$ preferably or in particular has that meaning which has already been indicated above, in connection with the description of the compounds of the formula (I), as being preferable or particularly preferable for $R^3$; X preferably represents fluorine, chlorine or bromine, and in particular represents chlorine.

The starting materials of the formula (VII) are known and/or can be prepared by methods known per se.

The processes (a), (b), (c) and (d) according to the invention for the preparation of the novel compounds of the formula (I) are preferably carried out using diluents. Suitable diluents in this context are virtually all inert organic solvents. These include, preferably, aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, tetrachloromethane, chlorobenzene and o-dichlorobenzene; ethers such as diethyl ether and dibutyl ether, glycol dimethyl ether and diglycol dimethyl ether, tetrahydrofuran and dioxane; ketones such as acetone, methyl ethyl ketone, methyl isopropyl ketone and methyl isobutyl ketone; esters such as methyl acetate and ethyl acetate; nitriles, for example acetonitrile and propionitrile; amides, for example dimethylformamide, dimethylacetamide and N-methylpyrrolidone, and also dimethyl sulphoxide, tetramethylene sulphone and hexamethylphosphoric triamide.

As reaction auxiliaries and/or as acid acceptors in the processes (a), (b), (c) and (d) according to the invention it is possible to employ all acid-binding agents which can customarily be used for such reactions. Preference is given to alkali metal hydroxides, for example sodium hydroxide and potassium hydroxide, alkaline earth metal hydroxides, for example calcium hydroxide, alkali metal carbonates and alkoxides, such as sodium carbonate and potassium carbonate, sodium tert-butoxide and potassium tert-butoxide, and also basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4.3.0]-non-5-ene (DBN), 1,8-diazabicyclo [5.4.0]-undec-7-ene (DBU) and 1,4-diazabicyclo-[2.2.2]-octane (DABCO).

The reaction temperatures in the processes (a), (b), (c) and (d) according to the invention can be varied within a relatively wide range. The reactions are in general carried out at temperatures of between −20° C. and +150° C., preferably at temperatures between 0° C. and +100° C.

The processes (a), (b), (c) and (d) according to the invention are generally carried out under atmospheric pressure. However, it is also possible to operate under elevated or reduced pressure.

For carrying out processes (a), (b), (c) and (d) according to the invention, the starting materials required in each case are in general employed in approximately equimolar quantities. However, it is also possible to use one of the components employed in each case in a relatively large excess. The reactions are in general carried out in a suitable diluent in the presence of an acid acceptor, and the reaction mixture is stirred for a number of hours at the particular temperature required. Work-up in the case of the processes (a), (b), (c) and (d) according to the invention is in each case carried out by customary methds (cf. the Preparation Examples).

Salts of the compounds of the general formula (I) according to the invention can be prepared if desired. Such salts are obtained in a simple manner by customary methods of forming salts, for example by dissolving or dispersing a compound of the formula (I) in an appropriate solvent, for example methylene chloride, acetone, tert-butyl methyl ether or toluene, and adding an appropriate base. The salts can then—if desired after prolonged stirring—be isolated by concentration or filtration with suction.

The active compounds according to the invention can be used as defoliants, desiccants, haulm killers and, especially, as weed-killers. By weeds, in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindemia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial crops, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective control of weeds in annual crops.

The compounds of the formula (I) according to the invention are preferably suitable for the selective control of monocotyledonous and dicotyledonous weeds in monocotyledonous and dicotyledonous crops, both pre-emergence and post-emergence.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. Suitable liquid solvents are in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam-forming agents are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersing agents are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 percent by weight of active compound, preferably between 0.5 and 90%.

For controlling weeds, the active compounds according to the invention, as such or in the form of their formulations, can also be used as mixtures with known herbicides, ready-to-use formulations or tank mixes being possible.

Possible components for the mixtures are known herbicides, for example anilides, such as diflufenican and propanil; arylcarboxylic acids, such as dichloropicolinic acid, dicamba and picloram; aryloxyalkanoic acids, such as 2,4-D, 2,4-DB, 2,4-DP, fluroxypyr, MCPA, MCPP and triclopyr; aryloxy-phenoxy-alkanoic esters, such as diclofop-methyl, fenoxaprop-ethyl, fluazifop-butyl, haloxyfop-methyl and quizalofop-ethyl; azinones, such as chloridazon and norflurazon; carbamates, such as chlorpropham, desmedipham, phenmedipham and propham; chloroacetanilides, such as alachlor, acetochlor, butachlor, metazachlor, metolachlor, pretilachlor and propachlor; dinitroanilines, such as oryzalin, pendimethalin and trifluralin; diphenyl ethers, such as acifluorfen, bifenox, fluoroglycofen, fomesafen, halosafen, lactofen and oxyfluorfen; ureas, such as chlorotoluron, diuron, fluometuron, isproturon, linuron and methabenzthiazuron; hydroxylamines, such as alloxydim, clethodim, cycloxydim, sethoxydim and tralkoxydim; imidazolinones, such as imazethapyr, imazamethabenz, imazapyr and imazaquin; nitriles, such as bromoxynil, dichlobenil and ioxynil; oxyacetamides, such as mefenacet; sulphonyl-ureas, such as amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates, such as butylate, cycloate, diallate, EPTC, esprocarb, molinate, prosulfocarb, thiobencarb and triallate; triazines, such as atrazine, cyanazine, simazine, simetryne, terbutryne and terbutylazine; triazinones, such as hexazinone, metamitron and metribuzin; others, such as aminotriazole, benfuresate, bentazone, cinmethylin, clomazone, clopyralid, defenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 10 g and 5 kg per ha.

The preparation and use of the active compounds according to the invention can be seen from the following examples.

PREPARATION EXAMPLES

Example 1

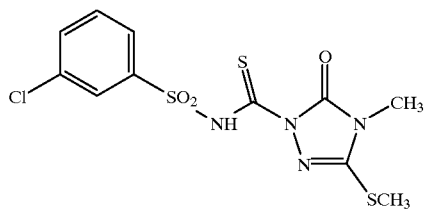

(by process (a))

A mixture of 3.0 g (20.7 mmol) of 4-methyl-5-methylthio-2,4-dihydro-3H-1,2,4-triazol-3-one, 4.8 g (20.7 mmol) of 3-chloro-phenylsulphonyl isothiocyanate, 0.3 g of triethylamine and 60 ml of acetonitrile is heated under reflux for 12 hours and then concentrated under water pump vacuum. The residue is stirred with diethyl ether and the crystalline product is isolated by filtration under suction.

2.1 g (27% of theory) of 2-(3-chloro-phenylsulphonyl-aminothiocarbonyl)-4-methyl-5-methylthio-2,4-dihydro-3H-1,2,4-triazol-3-one of melting point 141° C. are obtained.

Example 2

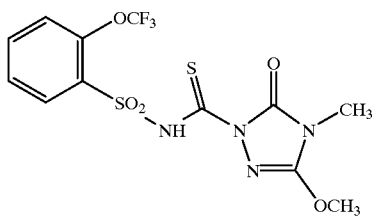

(by process (b))

A mixture of 3.2 g (12 mmol) of 5-methoxy-4-methyl-2-phenoxythiocarbonyl-2,4-dihydro-3H-1,2,4-triazol-3-one, 2.9 g (12 mmol) of 2-trifluoromethoxy-benzene-sulphonamide, 1.9 g (12.5 mmol) of 1,8-diazabicyclo-[5.4.0]-undec-7-ene (DBU) and 30 ml of dioxane is stirred at 20° C. for 12 hours. The mixture is then diluted with methylene chloride and water and the pH is adjusted to 3 using 2N hydrochloric acid. The organic phase is then separated off, dried with sodium sulphate and filtered. The filtrate is concentrated under a water pump vacuum, the residue is crystallized by digestion with diethyl ether and the product is isolated by filtration under suction.

3.1 g (63% of theory) of 5-methoxy-4-methyl-2-(2-trifluoromethoxy-phenylsulphonyl-aminothiocarbonyl)-2,4-dihydro-3H-1,2,4-triazol-3-one of melting point 139° C. are obtained.

Example 3

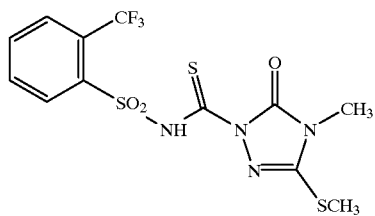

(by process (b))

At 20° C., 28.1 g (0.125 mol) of 2-trifluoromethyl-benzenesulphonamide and a solution of 19 g of 1,8-diazabicyclo-[5.4.0]-undec-7-ene (DBU) in 50 ml of acetonitrile are added in succession to a solution of 28.1 g (0.10 mol) of 4-methyl-5-methylthio-2-phenoxythiocarbonyl-2,4-dihydro-3H-1,2,4-triazol-3-one in 300 ml of acetonitrile. The reaction mixture is stirred at 20° C. until a clear solution is obtained. The solution is then concentrated under water pump vacuum and the residue is admixed with water and methylene chloride (300 ml each) and acidified with 2N hydrochloric acid. The organic phase is separated off, the aqueous phase is extracted once more with 100 ml of methylene chloride and the combined organic phases are dried with magnesium sulphate and filtered. The filtrate is concentrated under a water pump vacuum and the residue is crystallized from isopropanol.

29.6 g (72% of theory) of 4-methyl-5-methylthio-2-(2-trifluoromethyl-phenylsulphonyl-aminothiocarbonyl)-2,4-dihydro-3H-1,2,4-triazol-3-one of melting point 154° C. are obtained.

By the methods of Examples 1, 2 and 3 and in accordance with the general description of the preparation processes according to the invention, it is also possible to prepare, for example, the compounds of the formula (I) listed in Table 1 below.

(I)

$$\text{R}^3\text{–SO}_2\text{–NH–C(Q}^2\text{)–N–C(Q}^1\text{)–N(R}^1\text{)–C(R}^2\text{)=N}$$

TABLE 1

Examples of compounds of the formula (I)

| Ex. No. | $Q^1$ | $Q^2$ | $R^1$ | $R^2$ | $R^3$ | Melting point (° C.) |
|---|---|---|---|---|---|---|
| 4 | O | S | $CH_3$ | $OC_3H_7$ | 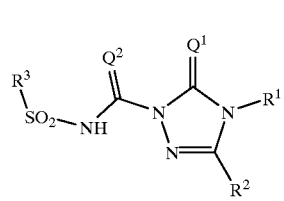 | 94 |

TABLE 1-continued

Examples of compounds of the formula (I)

| Ex. No. | Q¹ | Q² | R¹ | R² | R³ | Melting point (° C.) |
|---|---|---|---|---|---|---|
| 5 | S | O | $CH_3$ | $C_2H_5$ | 2-($CF_3$)-phenyl | 126 |
| 6 | O | S | $CH_3$ | $SCH_3$ | 4-Cl-phenyl | 142 |
| 7 | O | S | $CH_3$ | $SCH_3$ | 2-F-phenyl | 186 |
| 8 | O | S | $CH_3$ | $SCH_3$ | 2-Cl-phenyl | 174 |
| 9 | O | S | $CH_3$ | $SCH_3$ | 3-methyl-2-($COOC_2H_5$)-thiophen-yl | 196 |
| 10 | O | S | $CH_3$ | $SCH_3$ | 2-($CH_2CF_3$)-phenyl | 194 |
| 11 | O | S | $CH_3$ | $SCH_3$ | 2-Br-phenyl | 143 |
| 12 | O | S | $CH_3$ | $SCH_3$ | phenyl | 159 |
| 13 | O | S | $CH_3$ | $SCH_3$ | 2-$CH_3$-phenyl | 156 |
| 14 | O | S | $CH_3$ | $SCH_3$ | 2-$OCHF_2$-phenyl | 139 |

TABLE 1-continued
Examples of compounds of the formula (I)
| Ex. No. | Q¹ | Q² | R¹ | R² | R³ | Melting point (° C.) |
|---|---|---|---|---|---|---|
| 15 | O | S | CH₃ | SCH₃ | 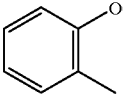 | 151 |
| 16 | O | S | CH₃ | SCH₃ | 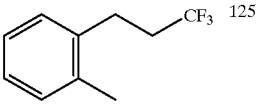 | 125 |
| 17 | O | S | CH₃ | SCH₃ | 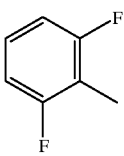 | 164 |
| 18 | O | S | CH₃ | SCH₃ | 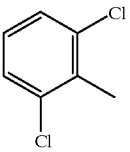 | 149 |
| 19 | O | S | CH₃ | SCH₃ | 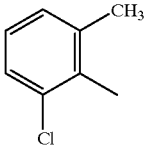 | 156 |
| 20 | O | S | CH₃ | SCH₃ | 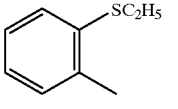 | 157 |
| 21 | O | S | CH₃ | SCH₃ | 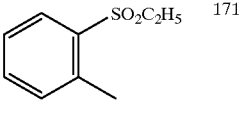 | 171 |
| 22 | O | S | CH₃ | SCH₃ | 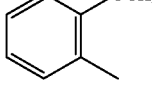 | 134 |
| 23 | O | S | CH₃ | SCH₃ | 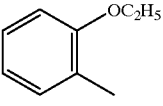 | 139 |

TABLE 1-continued
Examples of compounds of the formula (I)
| Ex. No. | $Q^1$ | $Q^2$ | $R^1$ | $R^2$ | $R^3$ | Melting point (° C.) |
|---|---|---|---|---|---|---|
| 24 | O | S | $CH_3$ | $SCH_3$ | 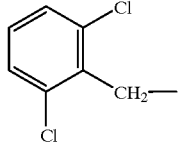 | 134 |
| 25 | O | S | $CH_3$ | $SCH_3$ | 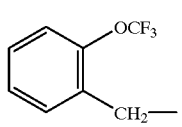 | 140 |
| 26 | O | S | $CH_3$ | $SCH_3$ | 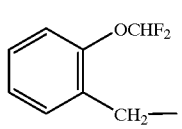 | 125 |
| 27 | O | S | $CH_3$ | $C_2H_5$ | 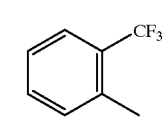 | 126 |
| 28 | O | S | $CH_3$ | $OC_2H_5$ | 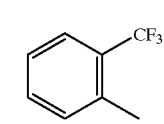 | 152 |
| 29 | O | S | $CH_3$ | $C_2H_5$ | 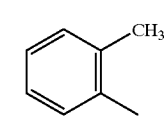 | 128 |
| 30 | O | S | $CH_3$ | $C_2H_5$ | 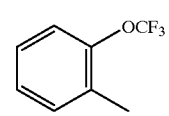 | 103 |
| 31 | O | S | $CH_3$ | $C_2H_5$ | 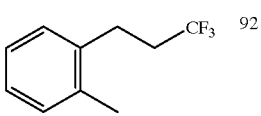 | 92 |
| 32 | O | S | $CH_3$ | $C_2H_5$ | 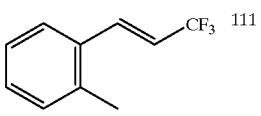 | 111 |

TABLE 1-continued
Examples of compounds of the formula (I)
| Ex. No. | Q¹ | Q² | R¹ | R² | R³ | Melting point (° C.) |
|---|---|---|---|---|---|---|
| 33 | O | S | CH$_3$ | C$_2$H$_5$ | 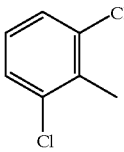 | 141 |
| 34 | O | S | CH$_3$ | OC$_2$H$_5$ | 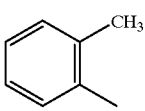 | 142 |
| 35 | O | S | CH$_3$ | OC$_2$H$_5$ | 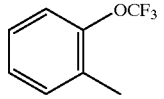 | 133 |
| 36 | O | S | CH$_3$ | OC$_2$H$_5$ | 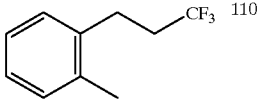 | 110 |
| 37 | O | S | CH$_3$ | OC$_2$H$_5$ | 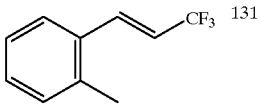 | 131 |
| 38 | O | S | CH$_3$ | OC$_2$H$_5$ | 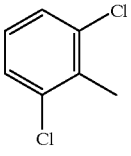 | 156 |
| 39 | O | S | CH$_3$ | OC$_2$H$_5$ | 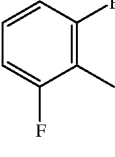 | 141 |
| 40 | O | S | CH$_3$ | OC$_2$H$_5$ | 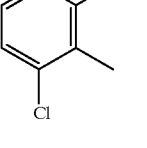 | 160 |
| 41 | O | S | CH$_3$ | OC$_2$H$_5$ | 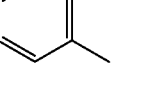 | 155 |

TABLE 1-continued
Examples of compounds of the formula (I)
| Ex. No. | Q¹ | Q² | R¹ | R² | R³ | Melting point (° C.) |
|---|---|---|---|---|---|---|
| 42 | O | S | CH₃ | OC₂H₅ | 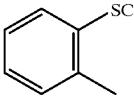 | 123 |
| 43 | O | S | CH₃ | OC₂H₅ | 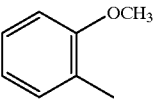 | 127 |
| 44 | O | S | CH₃ | OCH₃ | 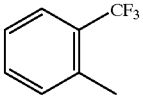 | 155 |
| 45 | O | S | —(CH₂)₅— | | 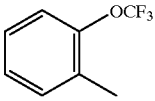 | 128 |
| 46 | O | S | CH₃ | OC₂H₅ | 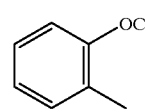 | 147 |
| 47 | O | S | OC₂H₅ | OC₂H₅ | 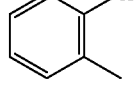 | 114 |
| 48 | O | S | OC₂H₅ | OC₂H₅ | 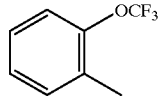 | 113 |
| 49 | O | S | N(CH₃)₂ | C₃H₇-n | 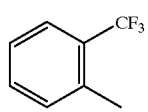 | 113 |
| 50 | O | S | N(CH₃)₂ | C₃H₇-n | 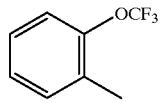 | 114 |
| 51 | O | S |  | OC₃H₇-i | 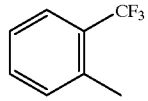 | 74 |

TABLE 1-continued
Examples of compounds of the formula (I)
| Ex. No. | Q¹ | Q² | R¹ | R² | R³ | Melting point (° C.) |
|---|---|---|---|---|---|---|
| 52 | O | S |  | OC$_3$H$_7$-i | 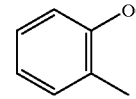 | 119 |
| 53 | O | S |  | N(CH$_3$)$_2$ | 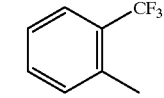 | 131 |
| 54 | O | S |  | N(CH$_3$)$_2$ | 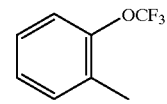 | 132 |
| 55 | O | S |  |  | 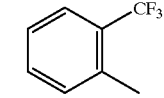 | 114 |
| 56 | O | S |  |  | 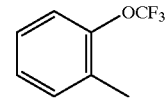 | 124 |
| 57 | O | S |  | SC$_2$H$_5$ | 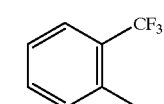 | 123 |
| 58 | O | S |  | SC$_2$H$_5$ | 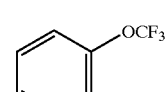 | 125 |
| 59 | O | S | OCH$_3$ | SCH$_3$ |  | 110 |
| 60 | O | S | OCH$_3$ | SCH$_3$ |  | 127 |
| 61 | O | S | OCH$_3$ | SC$_2$H$_5$ |  | 121 |

TABLE 1-continued

Examples of compounds of the formula (I)

| Ex. No. | Q¹ | Q² | R¹ | R² | R³ | Melting point (° C.) |
|---|---|---|---|---|---|---|
| 62 | O | S | OCH$_3$ | SC$_2$H$_5$ | 2-OCF$_3$, 6-methylphenyl | 122 |
| 63 | O | S | CH$_3$ | CH$_3$ | 2-CF$_3$, 6-methylphenyl | 119 |
| 64 | O | S | CH$_3$ | CH$_3$ | 2-OCF$_3$, 6-methylphenyl | 122 |
| 65 | O | S | CH$_3$ | CH$_3$ | 2-OCHF$_2$, 6-methylphenyl | 113 |
| 66 | O | S | CH$_3$ | C$_2$H$_5$ | 2-OCHF$_2$, 6-methylphenyl | 118 |
| 67 | O | S | CH$_3$ | C$_3$H$_7$-n | 2-CF$_3$, 6-methylphenyl | 112 |
| 68 | O | S | CH$_3$ | C$_3$H$_7$-n | 2-OCHF$_2$, 6-methylphenyl | 112 |
| 69 | O | S | CH$_3$ | C$_3$H$_7$-i | 2-CF$_3$, 6-methylphenyl | 119 |
| 70 | O | S | CH$_3$ | C$_3$H$_7$-i | 2-OCF$_3$, 6-methylphenyl | 101 |
| 71 | O | S | CH$_3$ | C$_3$H$_7$-i | 2-OCHF$_2$, 6-methylphenyl | 118 |

TABLE 1-continued
Examples of compounds of the formula (I)
| Ex. No. | $Q^1$ | $Q^2$ | $R^1$ | $R^2$ | $R^3$ | Melting point (° C.) |
|---|---|---|---|---|---|---|
| 72 | O | S | $CH_3$ | $CH_2OCH_3$ | 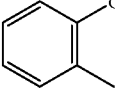 | 124 |
| 73 | O | S | $CH_3$ | $CH_2OCH_3$ | 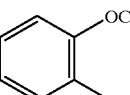 | 108 |
| 74 | O | S | $CH_3$ | $CH_2OCH_3$ | 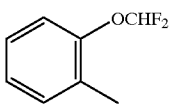 | 106 |
| 75 | O | S | $CH_3$ | $SC_2H_5$ | 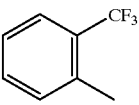 | 129 |
| 76 | O | S | $CH_3$ | $SC_2H_5$ | 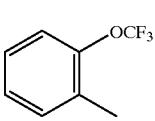 | 131 |
| 77 | O | S | $CH_3$ | $SC_2H_5$ | 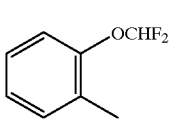 | 135 |
| 78 | O | S | $CH_3$ | $OCH_3$ | 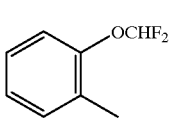 | 131 |
| 79 | O | S | $C_2H_5$ | $OC_2H_5$ | 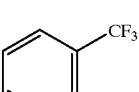 | 128 |
| 80 | O | S | $C_2H_5$ | $OC_2H_5$ | 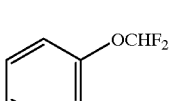 | 85 |
| 81 | O | S | $CH_3$ | $OC_3H_7$-n | 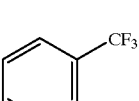 | 108 |

TABLE 1-continued

Examples of compounds of the formula (I)

| Ex. No. | $Q^1$ | $Q^2$ | $R^1$ | $R^2$ | $R^3$ | Melting point (° C.) |
|---|---|---|---|---|---|---|
| 82 | O | S | $CH_3$ | $OC_3H_7$-n | 2-$CF_3$, 6-methylphenyl | 122 |
| 83 | O | S | $CH_3$ | $OC_3H_7$-i | 2-$OCF_3$, 6-methylphenyl | 119 |
| 84 | O | S | $CH_3$ | $OC_3H_7$-i | 2-$OCHF_2$, 6-methylphenyl | 130 |
| 85 | O | S | $C_2H_5$ | $OCH_3$ | 2-$CF_3$, 6-methylphenyl | 123 |
| 86 | O | S | $C_2H_5$ | $OCH_3$ | 2-$OCHF_2$, 6-methylphenyl | 132 |
| 87 | O | S | $OC_2H_5$ | $C_2H_5$ | 2-$OCF_3$, 6-methylphenyl | 109 |
| 88 | O | S | $OC_2H_5$ | $C_2H_5$ | 2-$OCHF_2$, 6-methylphenyl | 105 |
| 89 | O | S | $CH_3$ | Br | 2-$CF_3$, 6-methylphenyl | 126 |
| 90 | O | S | $CH_3$ | Br | 2-$OCF_3$, 6-methylphenyl | 115 |
| 91 | O | S | $CH_3$ | Br | 2-$OCHF_2$, 6-methylphenyl | 113 |

TABLE 1-continued
Examples of compounds of the formula (I)
| Ex. No. | Q¹ | Q² | R¹ | R² | R³ | Melting point (° C.) |
|---|---|---|---|---|---|---|
| 92 | O | S |  | Br | 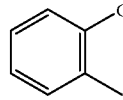 | 113 |
| 93 | O | S |  | Br | 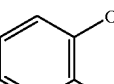 | 107 |
| 94 | O | S |  | Br | 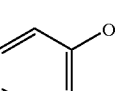 | 103 |
| 95 | O | S |  | OC$_2$H$_5$ | 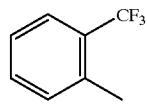 | 117 |
| 96 | O | S |  | OC$_2$H$_5$ | 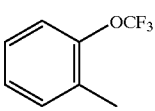 | 105 |
| 97 | O | S |  | OC$_2$H$_5$ | 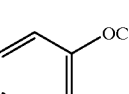 | 90 |
| 98 | O | S |  | CH$_2$OCH$_3$ | 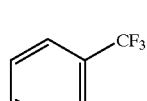 | 106 |
| 99 | O | S |  | CH$_2$OCH$_3$ | 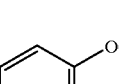 | 119 |
| 100 | O | S |  | CH$_2$OCH$_3$ | 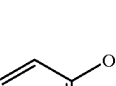 | 110 |
| 101 | O | S | CH$_3$ | C$_2$H$_5$ | 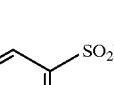 | 119 |

TABLE 1-continued

Examples of compounds of the formula (I)

| Ex. No. | Q¹ | Q² | R¹ | R² | R³ | Melting point (° C.) |
|---|---|---|---|---|---|---|
| 102 | O | S | $CH_3$ | $C_2H_5$ | 2-($SC_2H_5$)-6-methylphenyl | 126 |
| 103 | O | S | $CH_3$ | $C_2H_5$ | 2-($SO_2C_2H_5$)-6-methylphenyl | 122 |
| 104 | O | S | $CH_3$ | $C_2H_5$ | 2-($OCH_3$)-6-methylphenyl | 127 |
| 105 | O | S | $CH_3$ | $C_2H_5$ | 2-($OC_2H_5$)-6-methylphenyl | 129 |
| 106 | O | S | $CH_3$ | $OC_2H_5$ | 2-($SO_2N(CH_3)_2$)-6-methylphenyl | 137 |
| 107 | O | S | $CH_3$ | $OC_2H_5$ | 2-($SO_2C_2H_5$)-6-methylphenyl | 127 |
| 108 | O | S | $CH_3$ | $OC_2H_5$ | 2-($OC_2H_5$)-6-methylphenyl | 151 |
| 109 | O | S | $CH_3$ | $C_2H_5$ | 2,6-difluoro-3-methylphenyl | 141 |
| 110 | O | S | $CH_3$ | $C_2H_5$ | 3-chloro-2-methyl-(with $CH_3$) phenyl | 143 |

TABLE 1-continued

Examples of compounds of the formula (I)

| Ex. No. | Q¹ | Q² | R¹ | R² | R³ | Melting point (° C.) |
|---|---|---|---|---|---|---|
| 111 | O | S | $CH_3$ | $SCH_3$ | 2-phenylphenyl | 130 |
| 112 | O | S | $CH_3$ | $C_2H_5$ | 2-fluorophenyl | 128 |
| 113 | O | S | $CH_3$ | $C_2H_5$ | 3-chlorophenyl | 115 |
| 114 | O | S | $CH_3$ | $C_2H_5$ | 4-chlorophenyl | 108 |
| 115 | O | S | $CH_3$ | $C_2H_5$ | 2-bromophenyl | 129 |
| 116 | O | S | $CH_3$ | $C_2H_5$ | phenyl | 128 |
| 117 | O | S | $CH_3$ | $OC_2H_5$ | 2-fluorophenyl | 130 |
| 118 | O | S | $CH_3$ | $OC_2H_5$ | 3-chlorophenyl | 135 |
| 119 | O | S | $CH_3$ | $OC_2H_5$ | 4-chlorophenyl | 145 |

TABLE 1-continued

Examples of compounds of the formula (I)

| Ex. No. | $Q^1$ | $Q^2$ | $R^1$ | $R^2$ | $R^3$ | Melting point (°C.) |
|---|---|---|---|---|---|---|
| 120 | O | S | CH$_3$ | OC$_2$H$_5$ | 2-Br-C$_6$H$_4$- | 128 |
| 121 | O | S | CH$_3$ | OC$_2$H$_5$ | C$_6$H$_5$- | 121 |
| 122 | O | S | CH$_3$ | C$_2$H$_5$ | 2-CF$_3$-C$_6$H$_4$-CH$_2$- | 92 |
| 123 | O | S | CH$_3$ | C$_2$H$_5$ | 2-OCF$_3$-C$_6$H$_4$-CH$_2$- | 115 |
| 124 | O | S | CH$_3$ | OC$_2$H$_5$ | 2-CF$_3$-C$_6$H$_4$-CH$_2$- | 147 |
| 125 | O | S | CH$_3$ | OC$_2$H$_5$ | 2-OCF$_3$-C$_6$H$_4$-CH$_2$- | 132 |
| 126 | O | S | CH$_3$ | SCH$_3$ | 2-CF$_3$-C$_6$H$_4$-CH$_2$- | 138 |
| 127 | O | S | cyclopropyl | OC$_2$H$_5$ | 2-CH$_3$-C$_6$H$_4$- | 137 |
| 128 | O | S | cyclopropyl | OC$_2$H$_5$ | 2-SCH$_3$-C$_6$H$_4$- | 105 |
| 129 | O | S | cyclopropyl | OC$_2$H$_5$ | 2-OH-C$_6$H$_4$- | 122 |

TABLE 1-continued

Examples of compounds of the formula (I)

| Ex. No. | Q¹ | Q² | R¹ | R² | R³ | Melting point (° C.) |
|---|---|---|---|---|---|---|
| 130 | O | S | OC$_2$H$_5$ | C$_2$H$_5$ | 2-CF$_3$-phenyl | 102 |
| 131 | O | S | OC$_2$H$_5$ | C$_2$H$_5$ | 2-OH-phenyl | 97 |
| 132 | O | S | cyclopropyl | Br | 2-SCH$_3$-phenyl | 132 |
| 133 | O | S | OC$_2$H$_5$ | C$_2$H$_5$ | 2-CH$_3$-phenyl | — |
| 134 | O | S | OC$_2$H$_5$ | C$_2$H$_5$ | 2-SCH$_3$-phenyl | 112 |
| 135 | O | S | cyclopropyl | Br | 2-CH$_3$-phenyl | 118 |
| 136 | O | S | CH$_3$ | CH$_2$OCH$_3$ | 2-SCH$_3$-phenyl | 100 |
| 137 | O | S | cyclopropyl | Br | 2-OH-phenyl | — |
| 138 | O | S | CH$_3$ | CH$_2$OCH$_3$ | 2-CH$_3$-phenyl | — |
| 139 | O | S | CH$_3$ | OCH$_2$CF$_3$ | 2-CF$_3$-phenyl | 73 |

TABLE 1-continued

Examples of compounds of the formula (I)

| Ex. No. | Q¹ | Q² | R¹ | R² | R³ | Melting point (° C.) |
|---|---|---|---|---|---|---|
| 140 | O | S | $CH_3$ | $OCH_2CF_3$ | 2-($OCF_3$)-6-methylphenyl | 107 |
| 141 | O | S | $CH_3$ | $OCH_2CF_3$ | 2-($OCHF_2$)-6-methylphenyl | 116 |
| 142 | O | S | $CH_3$ | $OC_3H_7$-n | 2-($OCHF_2$)-6-methylphenyl | |
| 143 | O | S | $OCH_2H_5$ | $C_2H_5$ | 2-($OCF_3$)-6-methylphenyl | |
| 144 | O | S | $CH_3$ | $OC_2H_5$ | 2,6-dichlorobenzyl | |
| 145 | O | S | $C_2H_5$ | $OCH_3$ | 2-($OCF_3$)-6-methylphenyl | 143 |
| 146 | O | S | $OCH_3$ | $C_3H_7$-n | 2-($OCF_3$)-6-methylphenyl | 98 |
| 147 | O | S | $CH_3$ | $SCH_3$ | 2-($SC_2H_5$)-6-methylphenyl | 208 (Na salt) |
| 148 | O | S | $CH_3$ | $SCH_3$ | 2-($CF_3$)-6-methylphenyl | 237 (Na salt) |
| 149 | O | S | $CH_3$ | $OCH_3$ | 2-($CF_3$)-6-methylphenyl | 210 (Na salt) |

TABLE 1-continued

Examples of compounds of the formula (I)

| Ex. No. | Q¹ | Q² | R¹ | R² | R³ | Melting point (° C.) |
|---|---|---|---|---|---|---|
| 150 | O | S | CH₃ | OCH₃ | 2-OCF₃, 6-CH₃-phenyl | 216 (Na salt) |
| 151 | O | S | CH₃ | OC₂H₅ | 2-OCHF₂, 6-CH₃-phenyl | 211 (Na salt) |
| 152 | O | S | CH₃ | OC₃H₇-n | 2-OCF₃, 6-CH₃-phenyl | 217 (Na salt) |
| 153 | O | S | CH₃ | C₂H₅ | 2,6-diCl-phenyl-CH₂— | 40 |
| 154 | O | S | —CH₂CH=CH₂ | OC₂H₅ | 2-CH₃-phenyl | 130 |
| 155 | O | S | —CH₂CH=CH₂ | OC₂H₅ | 2-OCF₃, 6-CH₃-phenyl | 84 |
| 156 | O | S | —CH₂CH=CH₂ | OC₂H₅ | 2-CF₃, 6-CH₃-phenyl | 85 |
| 157 | O | S | cyclopropyl | OC₂H₅ | 2-OCHF₂, 6-CH₃-phenyl | 205 (Na salt) |
| 158 | O | S | cyclopropyl | Br | 2-OCHF₂, 6-CH₃-phenyl | 212 (Na salt) |
| 159 | O | S | cyclopropyl | Br | 2-OCF₃, 6-CH₃-phenyl | 220 (Na salt) |

TABLE 1-continued

Examples of compounds of the formula (I)

| Ex. No. | Q¹ | Q² | R¹ | R² | R³ | Melting point (° C.) |
|---|---|---|---|---|---|---|
| 160 | O | S |  | Br | 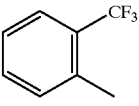 | 150 (Na salt) |
| 161 | O | S | CH₃ | —CH₂OCH₃ | 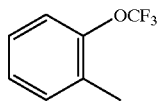 | 205 (Na salt) |
| 162 | O | S | CH₃ | —CH₂OCH₃ | 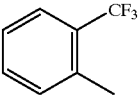 | 165 (Na salt) |
| 163 | O | S |  | OC₂H₅ | 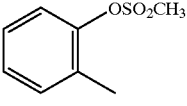 | 128 |
| 164 | O | S | OC₂H₅ | C₂H₅ | 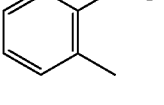 | 120 |

Starting materials of the formula (II):

Example (II-1)

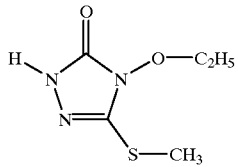

A mixture of 4.0 g (20 mmol) of the potassium salt of 4-ethoxy-5-mercapto-2,4-dihydro-3H-1,2,4-triazol-3-one, 4.3 g (30 mmol) of methyl iodide and 50 ml of methanol is stirred at 20° C. for 16 hours and then concentrated. The residue is extracted with methylene chloride/water and the organic phase is separated off, dried with magnesium sulphate and filtered. The filtrate is concentrated, the residue is digested with diethyl ether and the crystalline product is isolated by filtration under suction.

1.8 g (51%6+1 of theory) of 4-ethoxy-5-methylthio-2,4-dihydro-3H-1,2,4-triazol-3-one of melting point 99° C. are obtained.

By the methods of Example (II-1) and/or by other known methods (cf. the publications mentioned above), it is also possible to prepare, for example, the compounds of the formula (II) below:

4-methyl-, 4,5-dimethyl-, 4-methyl-5-ethyl-, 4-methyl-5-n-propyl-, 4-methyl-5-i-propyl-, 4-methyl-5-n-butyl-, 4-methyl-5-phenoxy-, 4-methyl-5-methylthio-, 4-methyl-5-ethylthio-, 4-methyl-5-n-propylthio-, 4-methyl-5-i-propylthio-, 4-methyl-5-allylthio-, 4-methyl-5-propargylthio-, 4-methyl-5-cyclopropyl-, 4-methyl-5-chloro-, 4-methyl-5-bromo-, 4-methyl-5-methoxy-, 4-methyl-5-ethoxy-, 4-methyl-5-n-propoxy-, 4-methyl-5-i-propoxy-, 4-methyl-5-n-butoxy-, 4-methyl-5-cyclopropylmethoxy-, 4-methyl-5-cyclopropylthio-, 4-methyl-5-trifluoroethoxy-,4-methyl-5-dimethylamino-and 4-methyl-5-methylamino- -2,4-dihydro-3H- 1,2,4-triazol-3-one and -2,4-dihydro-3H- 1,2,4-triazole-3-thione;

4-ethyl-, 4,5-diethyl-, 4-ethyl-5-methyl-, 4-ethyl-5-n-propyl-, 4-ethyl-5-i-propyl-, 4-ethyl-5-n-butyl-, 4-ethyl-5-phenoxy-, 4-ethyl-5-methylthio-, 4-ethyl-5-ethylthio-, 4-ethyl-5-n-propylthio-, 4-ethyl-5-i-propylthio-, 4-ethyl-5-allylthio-, 4-ethyl-5-propargylthio-, 4-ethyl-5-cyclopropyl-, 4-ethyl-5-chloro-, 4-ethyl-5-bromo-, 4-ethyl-5-methoxy-, 4-ethyl-5-ethoxy-, 4-ethyl-5-n-propoxy-, 4-ethyl-5-i-propoxy-, 4-ethyl-5-n-butoxy-, 4-ethyl-5-cyclopropylmethoxy-, 4-ethyl-5-cyclopropylthio-, 4-ethyl-5-trifluoroethoxy-,4-ethyl-5-dimethylamino-and 4-ethyl-5-methylamino-2,4-dihydro-3H-1,2,4-triazol-3-one and -2,4-dihydro-3H-1,2,4-triazole-3-thione;

4-cyclopropyl-5-methyl-, 4-cyclopropyl-5-ethyl-, 4-cyclopropyl-5-n-propyl-, 4-cyclopropyl-5-i-propyl-, 4-cyclopropyl-5-n-butyl-, 4-cyclopropyl-5-phenoxy-, 4-cyclopropyl-5-methylthio-, 4-cyclopropyl-5-ethylthio-, 4-cyclopropyl-5-n-propylthio-, 4-cyclopropyl-5-i-propylthio-,4-cyclopropyl-5-allylthio-,4-cyclopropyl-5-propargylthio-, 4-cyclopropyl-5-cyclopropyl-, 4-cyclopropyl-5-chloro-, 4-cyclopropyl-5-bromo-, 4-cyclopropyl-5-methoxy-, 4-cyclopropyl-5-ethoxy-, 4-cyclopropyl-5-n-propoxy-, 4-cyclopropyl-5-i-propoxy-, 4-cyclopropyl-5-n-butoxy-, 4-cyclopropyl-5-cyclopropylmethoxy-, 4-cyclopropyl-5-cyclopropylthio-, 4-cyclopropyl-5-trifluoroethoxy-, 4-cyclopropyl-5-dimethylamino- and 4-cyclopropyl-5-methylamino-2,4-dihydro-3H- 1,2,4-triazol-3-one and -2,4-dihydro-3H- 1,2,4-triazole-3-thione;

4-methoxy-, 4,5-dimethoxy-, 4-methoxy-5-methyl-, 4-methoxy-5-ethyl-, 4-methoxy-5-n-propyl-, 4-methoxy-5-i-propyl-, 4-methoxy-5-n-butyl-, 4-methoxy-5-phenoxy-, 4-methoxy-5-methylthio-, 4-methoxy-5-ethylthio-, 4-methoxy-5-n-propylthio-, 4-methoxy-5-i-propylthio-, 4-methoxy-5-allylthio-, 4-methoxy-5-propargylthio-, 4-methoxy-5-cyclopropyl-, 4-methoxy-5-chloro-, 4-methoxy-5-bromo-, 4-methoxy-5-ethoxy-, 4-methoxy-5-n-propoxy-, 4-methoxy-5-i-propoxy-, 4-methoxy-5-n-butoxy-, 4-methoxy-5-cyclopropylmethoxy-, 4-methoxy-5-cyclopropylthio-, 4-methoxy-5-trifluoroethoxy-, 4-methoxy-5-dimethylamino- and 4-methoxy-5-methylamino-2,4-dihydro-3H- 1,2,4-triazol-3-one and -2,4-dihydro-3H- 1,2,4-triazole-3-thione;

4-ethoxy-, 4,5-diethoxy-, 4-ethoxy-5-methyl-, 4-ethoxy-5-ethyl-, 4-ethoxy-5-n-propyl-, 4-ethoxy-5-i-propyl-, 4-ethoxy-5-n-butyl-, 4-ethoxy-5-phenoxy-, 4-ethoxy-5-methylthio-, 4-ethoxy-5-ethylthio-, 4-ethoxy-5-n-propylthio-, 4-ethoxy-5-i-propylthio-, 4-ethoxy-5-allylthio-, 4-ethoxy-5-propargylthio-, 4-ethoxy-5-cyclopropyl-, 4-ethoxy-5-chloro-, 4-ethoxy-5-bromo-, 4-ethoxy-5-methoxy-, 4-ethoxy-5-n-propoxy-, 4-ethoxy-5-i-propoxy-, 4-ethoxy-5-n-butoxy-, 4-ethoxy-5-cyclopropylmethoxy-, 4-ethoxy-5-cyclopropylthio-, 4-ethoxy-5-trifluoroethoxy-, 4-ethoxy-5-dimethylamino- and 4-ethoxy-5-methylamino--2,4-dihydro-3H- 1,2,4-triazol-3-one and -2,4-dihydro-3H- 1,2,4-triazole-3-thione;

4-amino-, 4-amino-5-methyl-, 4-amino-5-ethyl-, 4-amino-5-n-propyl-, 4-amino-5-i-propyl-, 4-amino-5-n-butyl-, 4-amino-5-phenoxy-, 4-amino-5-methylthio-, 4-amino-5-ethylthio-, 4-amino-5-n-propylthio-, 4-amino-5-i-propylthio-, 4-amino-5-allylthio-, 4-amino-5-propargylthio-, 4-amino-5-cyclopropyl-, 4-amino-5-chloro-, 4-amino-5-bromo-, 4-amino-5-methoxy-, 4-amino-5-ethoxy-, 4-amino-5-n-propoxy-, 4-amino-5-i-propoxy-, 4-amino-5-n-butoxy-, 4-amino-5-cyclopropylmethoxy-, 4-amino-5-cyclopropylthio-, 4-amino-5-trifluoroethoxy-, 4-amino-5-dimethylamino- and 4-amino-5-methylamino-2,4-dihydro-3H- 1,2,4-triazol-3-one and -2,4-dihydro-3H- 1,2,4-triazole-3-thione;

4-methylamino-,4-methylamino-5-methyl-,4-methylamino-5-ethyl-,4-methylamino-5-n-propyl-, 4-methylamino-5-i-propyl-, 4-methylamino-5-n-butyl-, 4-methylamino-5-phenoxy-, 4-methylamino-5-methylthio-, 4-methylamino-5-ethylthio-, 4-methylamino-5-n-propylthio-, 4-methylamino-5-i-propylthio-, 4-methylamino-5-allylthio-, 4-methylamino-5-propargylthio-, 4-methylamino-5-cyclopropyl-, 4-methylamino-5-chloro-, 4-methylamino-5-bromo-, 4-methylamino-5-methoxy-, 4-methylamino-5-ethoxy-, 4-methylamino-5-n-propoxy-,4-methylamino-5-i-propoxy-, 4-methylamino-5-n-butoxy-, 4-methylamino-5-cyclopropylmethoxy-, 4-methylamino-5-cyclopropylthio-, 4-methylamino-5-trifluoroethoxy-, 4-methylamino-5-dimethylamino- and 4-methylamino-5-methylamino- -2,4-dihydro-3H-1,2,4-triazol-3-one and -2,4-dihydro-3H- 1,2,4-triazole-3-thione;

4-dimethylamino-, 4-dimethylamino-5-methyl-, 4-dimethylamino-5-ethyl-, 4-dimethylamino-5-n-propyl-,4-dimethylamino-5-i-propyl-,4-dimethylamino-5-n-butyl-, 4-dimethylamino-5-phenoxy-, 4-dimethylamino-5-methylthio-, 4-dimethylamino-5-ethylthio-, 4-dimethylamino-5-n-propylthio-, 4-dimethylamino-5-i-propylthio-, 4-dimethylamino-5-allylthio-, 4-dimethylamino-5-propargylthio-, 4-dimethylamino-5-cyclopropyl-, 4-dimethylamino-5-chloro-,4-dimethylamino-5-bromo-,4-dimethylamino-5-methoxy-, 4-dimethylamino-5-ethoxy-, 4-dimethylamino-5-n-propoxy-, 4-dimethylamino-S-i-propoxy-, 4-dimethylamino-5-n-butoxy-, 4-dimethylamino-5-cyclopropylmethoxy-, 4-dimethylamino-5-cyclopropylthio-, 4-dimethylamino-5-trifluoroethoxy-, 4-dimethylamino-5-dimethylamino- and 4-dimethylamino-5-methylamino-2,4-dihydro-3H- 1,2,4-triazol-3-one and 2,4-dihydro-3H- 1,2,4-triazole-3-thione.

Starting materials of the formula (IV):

Example (IV-1)

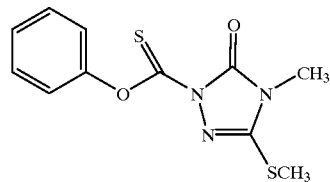

At 20° C., a solution of 15.0 g (103 mmol) of 4-methyl-5-methylthio-2,4-dihydro-3H-1,2,4-triazol-3-one in 120 ml of methylene chloride is admixed with a solution of 4.6 g of sodium hydroxide and 0.5 g of tetrabutylammonium bromide in 120 ml of water. A solution of 19.6 g (114 mmol) of O-phenyl chlorothioformate in 100 ml of methylene chloride is then added dropwise to this mixture at 20° C., and the reaction mixture is stirred at 20° C. for a further 12 hours. The crystalline product is isolated by filtration under suction.

25.6 g (88% of theory) of 4-methyl-5-methylthio-2-phenoxythiocarbonyl-2,4-dihydro-3H-1,2,4-triazol-3-one of melting point 242° C. are obtained.

Example (IV-2)

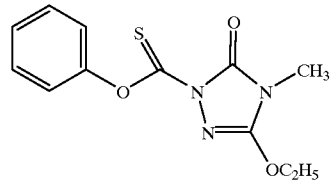

At 20° C., a solution of 29.6 g (206 mmol) of 4-methyl-5-ethoxy-2,4-dihydro-3H-1,2,4-triazol- 3-one in 240 ml of methylene chloride is admixed with a solution of 9.2 g of sodium hydroxide and 1 g of tetrabutylammonium bromide in 240 ml of water. A solution of 39.2 g (228 mmol) of O-phenyl chlorothioformate in 200 ml of methylene chloride is then added dropwise to this mixture at 20° C., and the reaction mixture is stirred at 20° C. for a further 12 hours. The organic phase is then separated off and the aqueous phase is extracted once more with 100 ml of methylene chloride. The combined organic phases are washed with 200 ml of water, dried with magnesium sulphate and filtered. The filtrate is concentrated under water pump vacuum, the residue is stirred with diethyl ether and the crystalline product is isolated by filtration under suction.

44.3 g (77% of theory) of 4-methyl-5-ethoxy-2-phenoxythiocarbonyl-2,4-dihydro-3H-1,2,4-triazol-3-one of melting point 123° C. are obtained.

By the methods of Examples (IV-1) and (IV-2), it is also possible to prepare, for example, the compounds of the formula (IV) listed in Table 2 below.

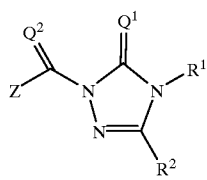

(IV)

TABLE 2

Examples of the compounds of the formula (IV)

| Ex. No. | $Q^1$ | $Q^2$ | $R^1$ | $R^2$ | Z | Melting point (° C.) |
|---|---|---|---|---|---|---|
| IV-3 | O | S | $CH_3$ | $C_2H_5$ | $OC_6H_5$ | 136 |
| IV-4 | O | S | $NH_2$ | $CH_3$ | $OC_6H_5$ | 177 |
| IV-5 | O | S | $NH_2$ | $N(CH_3)_2$ | $OC_6H_5$ | 161 |
| IV-6 | O | S | N=C(CH_3)(C_4H_9\text{-}n) | $N(CH_3)_2$ | $OC_6H_5$ | 92 |
| IV-7 | O | S | $NH_2$ | $OCH_3$ | $OC_6H_5$ | 158 |
| IV-8 | O | S | $CH_3$ | $OC_3H_7\text{-}n$ | $OC_6H_5$ | 90 |
| IV-9 | O | S | $CH_3$ | $OCH_3$ | $OC_6H_5$ | 186 |
| IV-10 | O | S | —$(CH_2)_5$— | | $OC_6H_5$ | 153 |
| IV-11 | O | S | cyclopropyl | $OC_2H_5$ | $OC_6H_5$ | 148 |
| IV-12 | O | S | $CH_3$ | $CH_3$ | $OC_6H_5$ | 139 |
| IV-13 | O | S | $OC_2H_5$ | $OC_2H_5$ | $OC_6H_5$ | 98 |
| IV-14 | O | S | $OCH_3$ | $SCH_3$ | $OC_6H_5$ | 180 |
| IV-15 | O | S | $OCH_3$ | $SC_2H_5$ | $OC_6H_5$ | 100 |
| IV-16 | O | S | $N(CH_3)_2$ | $C_3H_7\text{-}n$ | $OC_6H_5$ | 58 |
| IV-17 | O | S | cyclopropyl | $OC_3H_7\text{-}i$ | $OC_6H_5$ | 89 |
| IV-18 | O | S | cyclopropyl | $N(CH_3)_2$ | $OC_6H_5$ | 154 |
| IV-19 | O | S | cyclopropyl | cyclopropyl | $OC_6H_5$ | 144 |
| IV-20 | O | S | cyclopropyl | $S\text{-}C_2H_5$ | $OC_6H_5$ | 124 |
| IV-21 | O | S | $CH_3$ | $OC_3H_7\text{-}i$ | $OC_6H_5$ | 108 |
| IV-22 | O | S | $C_2H_5$ | $OCH_3$ | $OC_6H_5$ | 122 |
| IV-23 | O | S | $OC_2H_5$ | $C_2H_5$ | $OC_6H_5$ | 95 |
| IV-24 | O | S | $CH_3$ | Br | $OC_6H_5$ | 211 |
| IV-25 | O | S | $CH_3$ | $OCH_2CF_3$ | $OC_6H_5$ | 122 |
| IV-26 | O | S | $OCH_3$ | $C_3H_7\text{-}n$ | $OC_6H_5$ | oil |
| IV-27 | O | S | cyclopropyl | Br | $OC_6H_5$ | 172 |

TABLE 2-continued

Examples of the compounds of the formula (IV)

| Ex. No. | $Q^1$ | $Q^2$ | $R^1$ | $R^2$ | Z | Melting point (° C.) |
|---|---|---|---|---|---|---|
| IV-28 | O | S | cyclopropyl | $CH_2OCH_3$ | $OC_6H_5$ | 74 |
| IV-29 | O | S | $C_2H_5$ | $OC_2H_5$ | $OC_6H_5$ | 89 |
| IV-30 | O | S | $CH_3$ | $SO_2CH_3$ | $OC_6H_5$ | 196 |
| IV-31 | O | S | $CH_3$ | $C_3H_7\text{-}n$ | $OC_6H_5$ | 67 |
| IV-32 | O | S | $CH_3$ | $C_3H_7\text{-}i$ | $OC_6H_5$ | 96 |
| IV-33 | O | S | $CH_3$ | $CH_2OCH_3$ | $OC_6H_5$ | 98 |
| IV-34 | O | S | $CH_3$ | $SC_2H_5$ | $OC_6H_5$ | 130 |
| IV-35 | O | S | $CH_2\text{—}CH\text{=}CH_2$ | $OC_2H_5$ | $OC_6H_5$ | |
| IV-36 | S | O | $CH_3$ | H | $OC_6H_5$ | 172 |

USE EXAMPLES

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is watered with the preparation of the active compound. It is advantageous to keep constant the amount of water per unit area. The concentration of the active compound in the preparation is of no importance, only the amount of active compound applied per unit area being decisive.

After three weeks, the degree of damage to the plants is rated in % damage in comparison to the development of the untreated control.

The figures denote:

0%=no action (like untreated control)

100%=total destruction

In this test, the compounds according to Preparation Examples 3, 23, 27 and 28, for example, exhibit a very strong action against weeds, while some of them are very well tolerated by crops, such as cotton.

TABLE A

Pre-emergence test/greenhouse

| Active compound | Application rate (g/ha) | Cotton | Echino chloa | Poa | Setaria | Portu- laca | Sola- num |
|---|---|---|---|---|---|---|---|
| (3) 2-CF₃-C₆H₄-SO₂-NH-C(=S)-N(triazolinone, N-CH₃, 3-SCH₃, 5-oxo) | 60 | 0 | 95 | 95 | 90 | 95 | 95 |
| (23) 2-OC₂H₅-C₆H₄-SO₂-NH-C(=S)-N(triazolinone, N-CH₃, 3-SCH₃, 5-oxo) | 60 | 0 | 80 | 95 | 90 | 70 | 90 |
| (27) 2-CF₃-C₆H₄-SO₂-NH-C(=S)-N(triazolinone, N-CH₃, 3-C₂H₅, 5-oxo) | 60 | 0 | 95 | 95 | 95 | 90 | 90 |
| (28) 2-CF₃-C₆H₄-SO₂-NH-C(=S)-N(triazolinone, N-CH₃, 3-OC₂H₅, 5-oxo) | 60 | 0 | 95 | 95 | 95 | 95 | 95 |

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the particular amounts of active compound desired are employed in 1000 l of water/ha.

After three weeks, the degree of damage to the plants is rated in % damage in comparison to the development of the untreated control.

The figures denote:

0%=no action (like untreated control)

100%=total destruction

In this test, the compounds of Preparation Examples 3, 15 and 28, for example, exhibit a very strong action against weeds, while being well tolerated by crops, such as wheat.

TABLE B

Post-emergence test/greenhouse

| Active compound | Application rate (g/ha) | Wheat | Amaranthus | Helianthus | Solanum | Xanthium |
|---|---|---|---|---|---|---|
| 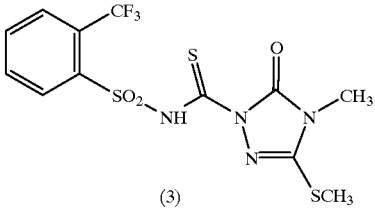 (3) | 60 | 5 | 95 | 100 | 90 | 95 |
| 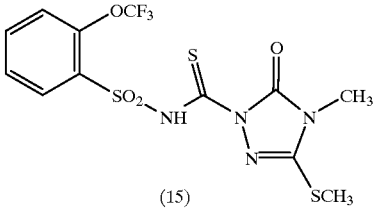 (15) | 60 | 0 | 85 | 95 | 85 | 70 |
| 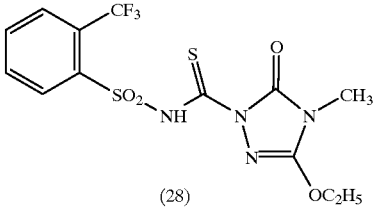 (28) | 60 | 10 | 95 | 100 | 99 | 90 |

What is claimed is:

1. A sulphonylamino(thio)carbonyl-triazolin(ethi)one compound of the general formula (I)

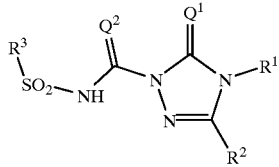

in which $Q^1$ represents oxygen, $Q^2$ represents sulphur, $R^1$ represents $C_1$–$C_6$-alkyl, or represents $C_2$–$C_6$-alkenyl, or represents $C_3$–$C_6$-cycloalkyl, $R^2$ represents $C_1$–$C_4$-alkoxy-substituted $C_1$–$C_6$-alkyl, or represents optionally fluorine substituted $C_1$–$C_6$-alkoxy, or represents $C_1$–$C_6$-alkylthio, or represents di-($C_1$–$C_4$-alkyl)-amino, $C_3$–$C_6$-cycloalkyl, $R^3$ represents the grouping

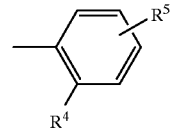

in which $R^4$ is identical or different and each represenst hydrogen, fluorine, chlorine, bromine, $C_1$–$C_6$-alkyl (which is optionally substituted by fluorine), or represents $C_2$–$C_6$-alkinyl (which is optionally substituted by fluorine), or represents $C_1$–$C_4$-alkoxy (which is optionally substituted by fluorine), $C_1$–$C_4$-alkylthio or represents the radical —$S(O)_p$—$R^6$ in which p represents the number 2 and $R^6$ represents $C_1$–$C_4$-alkyl, di-($C_1$–$C_4$-alkyl)-amino $R^4$ further represents phenyl $R^5$ represents hydrogen and the sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzyl-ammonium salt thereof.

2. Compounds of the formula (I) according to claim 1, wherein $Q^1$ represents oxygen, $Q^2$ represents sulphur, $R^1$ represents optionally ethoxy-substituted methyl, ethyl, propenyl, cyclopropyl, $R^2$ represents hydrogen, or represents optionally methoxy-substituted methyl, ethyl, n or i propyl, or represents respectively optionally fluorine-substituted methoxy, ethoxy, n- or i-propoxy, methylthio, ethylthio, or represents dimethylamino, or represents cyclopropyl, $R^3$ represents the radical

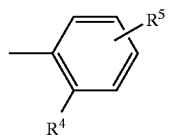

in which $R^4$ represents fluorine, chlorine or bromine, or represents optionally fluorine-substituted methyl, or represents optionally fluorine-substituted methoxy, methylthio, methylsulphonyl, ethylsulphonyl, dimethylaminosulfonyl, phenyl, and $R^5$ represents hydrogen.

3. An herbicidal composition which comprises an herbicidally effective amount of a compound according to claim 1 and an inert carrier.

4. A method of combatting unwanted plant growth which comprises applying to said unwanted plant or to an environment in which it is desired to exclude said unwanted plant an herbidically effective amount of a compound according to claim 1.

* * * * *

UNITED STATES PATENT AND TRADEMARK OFFICE
CERTIFICATE OF CORRECTION

PATENT NO. : 5,972,844 Page 1 of 1
DATED : October 26, 1999
INVENTOR(S) : Muller et al.

It is certified that error appears in the above-identified patent and that said Letters Patent is hereby corrected as shown below:

Column 62,
Line 47, "represenst" should read -- represents --.

Signed and Sealed this

Second Day of November, 2004

JON W. DUDAS
*Director of the United States Patent and Trademark Office*